(12) United States Patent
McFall et al.

(10) Patent No.: US 6,203,654 B1
(45) Date of Patent: Mar. 20, 2001

(54) METHOD OF MAKING A SLITTED OR PARTICULATE ABSORBENT MATERIAL

(75) Inventors: Ronald Ray McFall; Gary Dean Lavon, both of West Chester; Wilfried Maria Kollner; John Richard Noel, both of Cincinnati; John Lee Hammons, Hamilton, all of OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/027,379

(22) Filed: Feb. 20, 1998

(51) Int. Cl.[7] ..................................................... B32B 31/00
(52) U.S. Cl. .......................... 156/268; 156/201; 156/202; 156/204; 156/216; 156/227; 156/257; 156/270; 156/308.2; 156/308.4; 225/97; 225/103; 604/378; 604/383; 604/385.01
(58) Field of Search .................................. 604/385.1, 378, 604/383, 385.01; 156/227, 201, 204, 202, 216, 256, 269, 270, 73.1, 308.2, 308.4, 290, 292, 268, 257; 225/97, 103, 104

(56) References Cited

U.S. PATENT DOCUMENTS

| 2,252,363 | * | 8/1941 | Carus | ...................................... | 225/97 |
| 3,459,274 | * | 8/1969 | Mac Phail | ............................. | 181/291 |
| 4,369,567 | * | 1/1983 | Bosch et al. | ............................. | 29/607 |
| 5,028,293 | * | 7/1991 | Harvey | .................................. | 156/449 |
| 5,038,989 | * | 8/1991 | Beliveau | ................................ | 225/93 |

\* cited by examiner

*Primary Examiner*—Linda Gray
(74) *Attorney, Agent, or Firm*—Jeffrey V. Bamber; Ingrid N. Hickman

(57) ABSTRACT

A method of making a slitted or particulate absorbent material for an absorbent article such as sanitary napkins, diapers, incontinence devices, and the like. The method can be carried out in situ on another component of the absorbent article in a manufacturing process without cutting the other component. In one embodiment, the absorbent material is placed between two carrier webs, and a force is applied to the composite of the absorbent material and the carrier webs. The force breaks the absorbent material, but only deforms the carrier webs to provide a self-contained web of particulate material between two carrier webs.

28 Claims, 10 Drawing Sheets

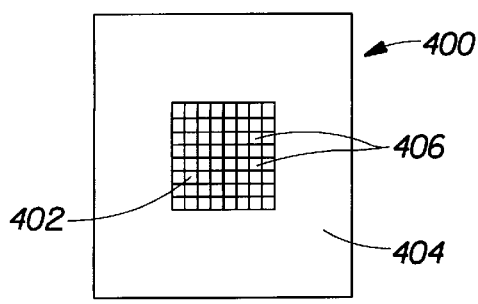
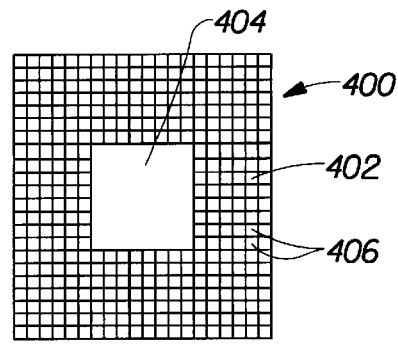
Fig. 4　　　　　Fig. 4A
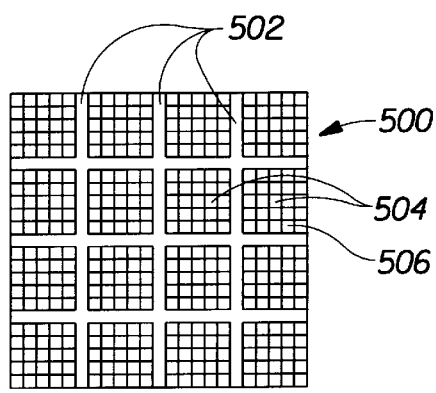
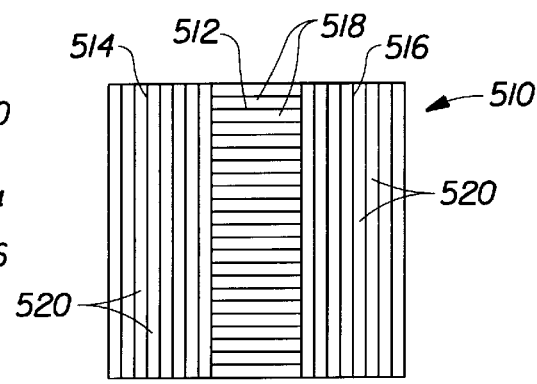
Fig. 5　　　　　Fig. 5A
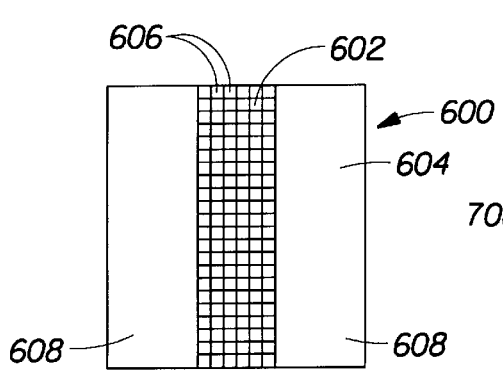
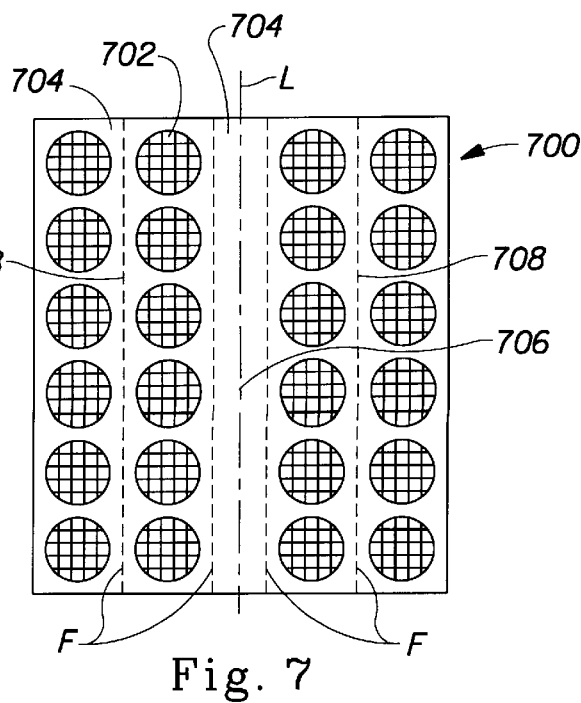
Fig. 6　　　　　Fig. 7

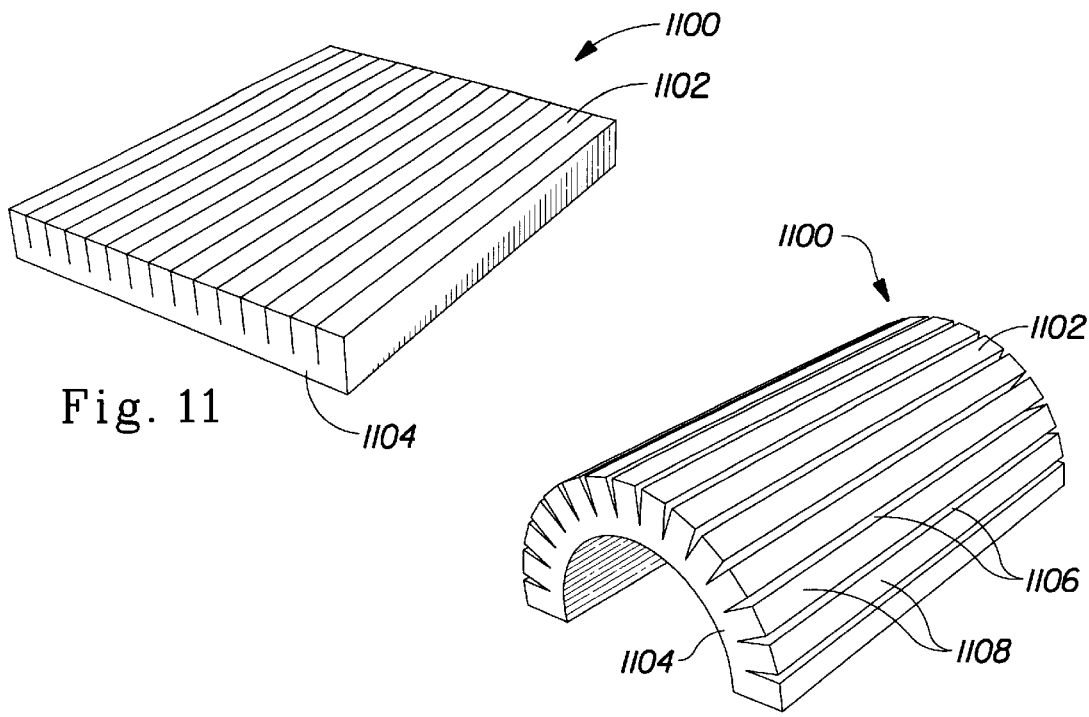
Fig. 11
Fig. 11A
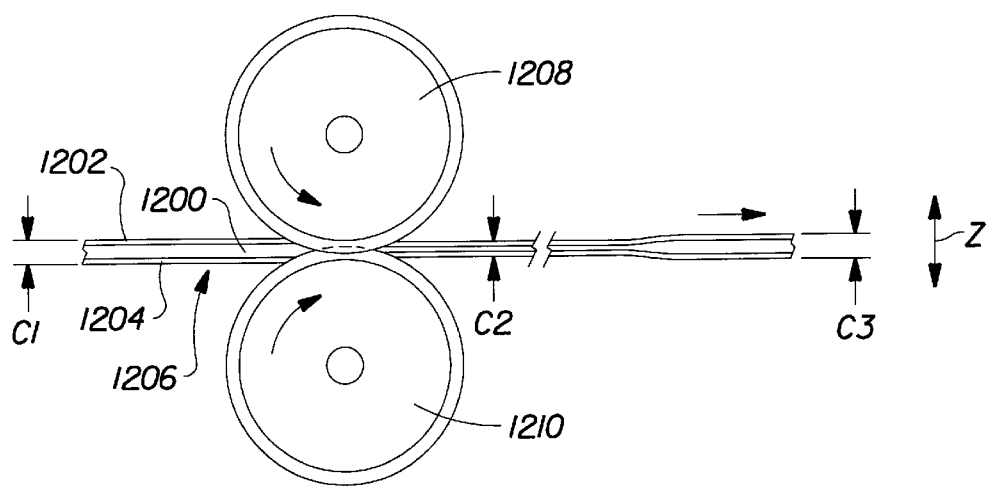
Fig. 12

US 6,203,654 B1

METHOD OF MAKING A SLITTED OR PARTICULATE ABSORBENT MATERIAL

FIELD OF THE INVENTION

The present invention relates to a method of making a slitted or particulate absorbent material for absorbent articles such as sanitary napkins, panty liners, absorbent interlabial devices, diapers, incontinence devices, tampons, bandages, wipes, and the like. More particularly, the present invention relates to a method as described above which can be carried out in situ on another component of the absorbent article in a manufacturing process, and can be accomplished without cutting the other component unless it is desired to do so. The present invention also relates to absorbent structures formed by this method.

BACKGROUND OF THE INVENTION

Absorbent articles such as sanitary napkins, pantiliners, disposable diapers, incontinence products, and bandages are designed to absorb and retain liquid and other discharges from the human body and to prevent body and clothing soiling. Absorbent articles typically comprise a liquid pervious topsheet, a liquid impervious backsheet, and an absorbent core positioned between the topsheet and backsheet. The absorbent core of absorbent articles currently in use can comprise a variety of different types of absorbent materials, including comminuted wood pulp, commonly known as airfelt, creped cellulose wadding; meltblown polymers including conform; chemically stiffened, modified or cross-linked cellulosic fibers; synthetic fibers such as crimped polyester fibers; peat moss; tissue including tissue wraps and tissue laminates; absorbent foams; absorbent sponges; super absorbent polymers; absorbent gelling materials; or any equivalent material or combinations of materials, or mixtures of these.

In some cases, it has been proposed to slit absorbent material for various purposes. Various methods of slitting materials for different purposes and slit articles are described in the patent literature. European Patent Application 0 234 194 published on Sep. 2, 1987, discloses a method and apparatus for providing sanitary goods with attachment means for attaching to under-clothing which involves slitting a soft and elastic plastic foam sheet. European Patent Specification 0 293 208 B1 discloses forming fluid absorptive material for a catamenial napkin or disposable diaper from a laminate of compressed cellulose-based sponge sheets that have slits provided therein. U.S. Pat. No. 5,397,316 issued to LaVon, et al. discloses absorbent members made of absorbent foam materials that remain relatively thin until wetted which are provided with slitted regions. U.S. Pat. No. 5,611,790 issued to Osborn, et al. discloses extensible absorbent articles which can have an absorbent core that is provided with slits therein.

Known methods of slitting, however, are typically impression related. In such methods, the slitting is done by placing the material to be slit between a sharp cutting blade and a hard backing surface, and cutting the material against the backing surface by applying pressure against the backing surface.

Impression related slitting methods suffer from several drawbacks. The cutting blade will have a high tendency to wear out, particularly if there is metal-to metal contact between the cutting blade and the backing surface. In addition, with impression related slitting, it is difficult to create narrow strips of slit material (for example, less than ½ inch (1.3 cm) wide strips of material) due to the difficulty in arranging the cutting blades sufficiently close together to create such narrow strips. Another disadvantage is that there are limitations to the location of the slitting operation in the process of making an absorbent article. It is generally difficult to slit a web of material after it is combined with another web of material without slitting both materials. While it is possible to slit only one web of such a combined web, great care has to be taken in setting the distance between the cutting blade and the backing surface so that only one of the webs is slit.

It has also been proposed to use particulate absorbent material in absorbent articles. However, the only known methods for providing a particulate absorbent material for an absorbent core involve a step of chopping the absorbent material to form particulate absorbent material, then transferring the chopped absorbent material to a delivery system for delivering the absorbent material to the absorbent core, providing a suitable receptacle to contain the particulate absorbent material, and delivering the chopped absorbent material to the receptacle.

Often, the delivery system for providing particulate absorbent material will involve mixing the particulate material in a stream of air and using the air to blow the particulate material into the receptacle for the absorbent material. This will generally require that the receptacle be closed on all sides to prevent the particles from being blown outside the receptacle. It will also require that the quantity of the absorbent material particles delivered to the absorbent article be controlled (or "metered").

These known methods for providing particulate absorbent material suffer from numerous drawbacks. They involve a substantial number of steps. They require the use of a delivery system, which typically must be a closed system so that the particles can be mixed in a stream of air. They require a supply of compressed air, and a closed receptacle to receive the particulate material.

Thus, a need exists for an improved method of making and providing a slitted or particulate absorbent material for absorbent articles.

SUMMARY OF THE INVENTION

The present invention is directed to a method of making a slitted or particulate absorbent material for an absorbent article such as sanitary napkins, diapers, incontinence devices, tampons, bandages, wipes, and the like. More particularly, the present invention relates to a method as described above which can be carried out in situ on another component of the absorbent article in a manufacturing process, and can be accomplished without cutting the other component unless it is desired to do so.

The present invention can be used even more broadly to break (fracture, fragment, or otherwise alter the integrity of) an absorbent material. This is particularly the case if it is not necessary to slit the material along pre-defined lines or to form the absorbent material into particulate material. The method of the present invention can break an absorbent material in a composite web without breaking the outer carrier web(s) by the application of a force on the composite web. The force applied to the composite web can be a tensile force, a compressive force, or both. If both of these types of forces are used, they can be applied either simultaneously, or sequentially (in either order). A large number of different processes and types of apparatus can be used to apply the force to the composite web. Suitable types of processes include, but are not limited to passing the composite web through a nip between grooved or patterned rolls, embossing (against a rigid or deformable surface), compression between mating plates, vacuum, or other methods for exerting a force on a material.

In one preferred embodiment, the method of making a slitted or particulate absorbent material comprises the steps of:

(a) providing a carrier web having a first breaking point;
(b) providing a second material on the carrier web to form a composite web having two surfaces, which second material has a second breaking point that is lower than the breaking point of the carrier web, and comprises an absorbent material;
(c) providing an apparatus for applying localized forces on portions of the composite web; and
(d) applying a force to at least a portion of at least one of the surfaces of the composite web using the apparatus, which force is greater than the second breaking point, but less than the first breaking point so that the second material breaks in at least one place without breaking the carrier web.

In a particularly preferred embodiment, the absorbent material is an absorbent foam that is wrapped inside a nonwoven carrier web. The force applied by the apparatus breaks the inner absorbent material (due to its greater destructibility), but only deforms the outer nonwoven web to provide a self-contained web of particulate material inside a nonwoven wrapping. The present invention provides an improved method of making and providing a self-contained slitted or particulate absorbent material for absorbent articles. The method of the present invention involves very few steps and significantly less additional equipment, and does not require a delivery system that uses compressed air to transport particulate material to a closed receptacle. The method of the present invention also eliminates the need to re-meter the quantity of the particulate material delivered to the absorbent article.

The present invention also relates to absorbent structures formed by this method. In one embodiment, the absorbent structure comprises a composite web of discrete elements of absorbent material. The composite web comprises at least one carrier web and a plurality of discrete elements of absorbent material arranged in an orderly array on the carrier web. In such an embodiment, the discrete elements of absorbent material can be positioned adjacent to each other without any intervening material between the discrete elements of absorbent material. In other embodiments, portions of the carrier web can be extended down between the discrete elements of absorbent material. In these or other embodiments, the composite absorbent structure can be extensible, stretchable, and/or elastically extensible. The absorbent structures of the present invention provide numerous advantages. These include, but are not limited to: providing a composite structure with improved flexibility and/or conformability to a wearer's body; improving the softness of the structure; improving the distribution of particulate absorbent material within the structure; and, improving the acquisition and handling of bodily fluids.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which:

FIG. 4 shows a web made according to one variation of the present invention which is provided with a central zone which is slit or formed into particulate material and a surrounding zone which is not slit or formed into particulate material.

FIG. 4A shows a web made according to another variation which is provided with a central zone that is not slit or formed into particulate material and a surrounding zone that is slit or formed into particulate material.

FIG. 5 shows a web made according to another variation of the present invention which is provided with a plurality of bands which are not slit or formed into particulate material that separate zones which are slit or formed into particulate material.

FIG. 5A shows a web made according to another variation of the present invention which is provided a longitudinal central region with slits oriented in the transverse direction and longitudinal side regions with slits oriented in the longitudinal direction.

FIG. 6 shows a composite absorbent structure made by the method of the present invention in which an additional strip of absorbent material is positioned on top of a continuous layer of absorbent material, and the composite absorbent structure is formed into particulate material in the region of the strip of material.

FIG. 7 shows a web of material that has circular portions therein that have been slit or formed into particulate material, and portions that have been unformed, in which the regions are arranged in a pattern where unformed portions will form a plurality of spring-like structures when the web is folded.

FIG. 11 shows a web of material similar to that shown in FIG. 10; however, in FIG. 11, only a portion of the surface on one side of the web of material is slit.

FIG. 11A shows an example of a structure that the web of material shown in FIG. 11 can be formed into when it is bent into an arcuate configuration.

FIG. 12 is a schematic side view that shows layers of a composite web that are combined by straining the composite web so that the fibers of the fibrous outer layers entangle the foam inner layer.

DETAILED DESCRIPTION OF THE INVENTION

Figure 1:
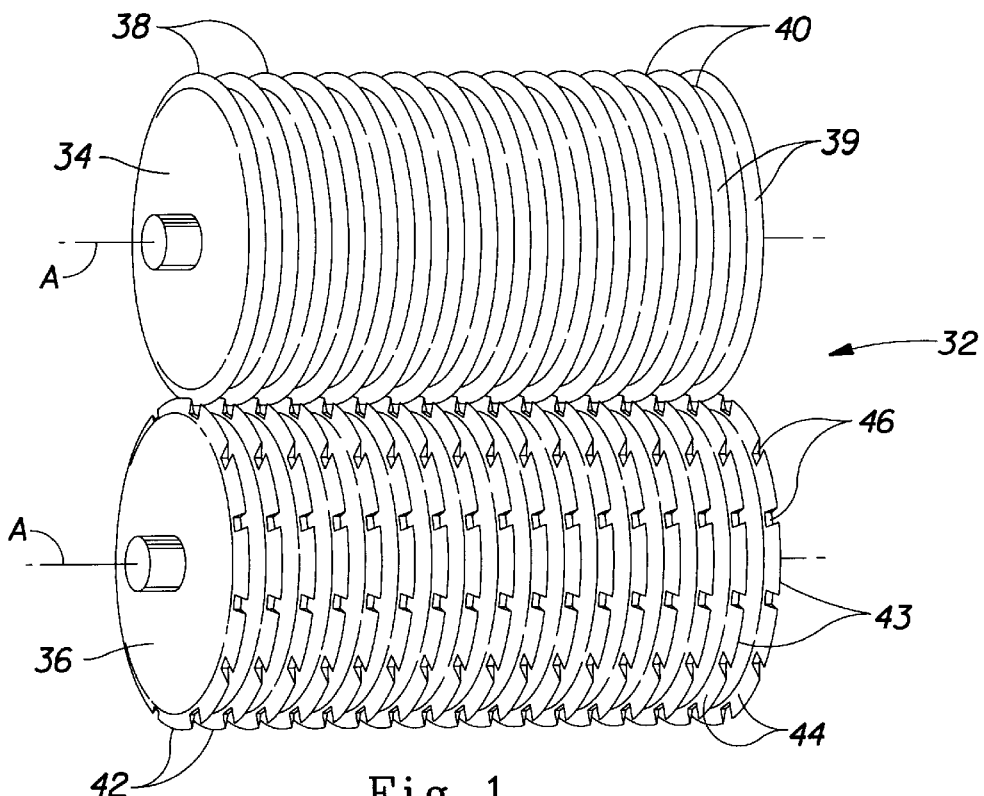
FIG. 1 is a simplified perspective view of one portion of apparatus that could be used to carry out the method of the present invention.

The present invention in a preferred embodiment, relates to a method of making a slitted or particulate absorbent material for an absorbent article such as sanitary napkins, panty liners, absorbent interlabial devices, diapers, incontinence devices, tampons, bandages, wipes, and the like. More particularly, the present invention relates to a method as described above which is preferably carried out in situ on another component of the absorbent article in a manufacturing process, and can be accomplished without cutting the other component, unless it is desired to do so.

The present invention can be used even more broadly to break (fracture, fragment, or otherwise alter the integrity of) an absorbent material. This is particularly the case if it is not necessary to slit the material along pre-defined lines or to form the absorbent material into particulate material. In preferred embodiments, the absorbent material may be positioned inside the composite web and the carrier web(s) positioned on the outside of the composite web. The method of the present invention can break the absorbent material in the composite web, without breaking the carrier web by the application of a force on the composite web. This is due to the greater destructibility of the absorbent material compared to that of the carrier web or webs. The force applied to the composite web can be a tensile force, compressive force, a force which is partially tensile and partially compressive, or both tensile and compressive forces (either simultaneously, or sequentially (in either order)).

Versions of the method of the present invention that apply only compressive forces to the composite web will not tend to stretch the carrier web(s), as will versions of the method of the present invention that apply at least some tensile forces. A tensile force component is preferred if it is desirable to create space between the broken portions (i.e., the pieces) of the absorbent material. Providing space between the pieces of the absorbent material may be desirable for acquisition of liquids into the absorbent material; creating spaces to extend portions of the carrier web down in between the pieces of absorbent material; creating spaces between the pieces for localized bonding one of the carrier webs to the other; and/or forming the absorbent material into different shapes (such as hourglass shaped webs).

In other words, the method of the present invention provides the ability to at least partially fracture a material without fracturing a material placed adjacent thereto. The expression "partially fractured", as used herein, refers to partial breaking, disrupting the integrity of, or producing discontinuities in the material in issue. The term "break", as used herein, refers to a more significant fracture such as where the material is severed and the portions of the material adjacent to the break separate. The material that is at least partially fractured is preferably absorbent. The other material may be deformed (e.g., corrugated and/or permanently elongated), but in the usual embodiment described herein, retains its structural integrity and is not disrupted (i.e., it remains in an integral condition). The materials described herein may be in many different forms. In preferred embodiments, the materials are in the form of two (or more) layers. These materials differ in their response to compressive forces and/or forces acting to elongate the materials.

A large number of different processes and types of apparatuses can be used to apply the force to the composite web. Suitable types of processes include, but are not limited to passing the composite web through a nip between grooved or patterned rolls—a process which has been described as pre-corrugating (or "ring rolling"); embossing (against a rigid or deformable surface), compression between mating plates; vacuum; or other methods for exerting a force on a material. Suitable methods for ring rolling are described in U.S. Pat. No. 4,107,364 issued to Sisson on Aug. 15, 1978, U.S. Pat. No. 5,143,679 issued to Gerald M. Weber, et al. on Sep. 1, 1992, U.S. Pat. No. 5,156,793 issued to Kenneth B. Buell, et al. on Oct. 20, 1992, and U.S. Pat. No. 5,167,897 issued to Gerald M. Weber, et al. on Dec. 1, 1992.

The term "patterned", as used herein with reference to a portion of the apparatus used in the method, refers to a surface with protrusions or depressions thereon (e.g., a relief or intaglio pattern). The apparatus used in the present invention is not limited to those having regular or repeating patterns thereon. If an apparatus with an element having a patterned surface is used, any suitable pattern that is capable of breaking the absorbent material can be used. The pattern can be regular or irregular (e.g., random). Regardless of the specific process or apparatus used, the method of the present invention is directed to the application of a concentrated force sufficiently high to cause localized failure in the absorbent material. The method of the present invention preferably breaks or fractures the absorbent material completely through, but in certain embodiments of the present invention, it need not. Preferably, the method of the present invention does not break the carrier web(s), but variations of the present invention are not precluded from doing so.

Figure 2:
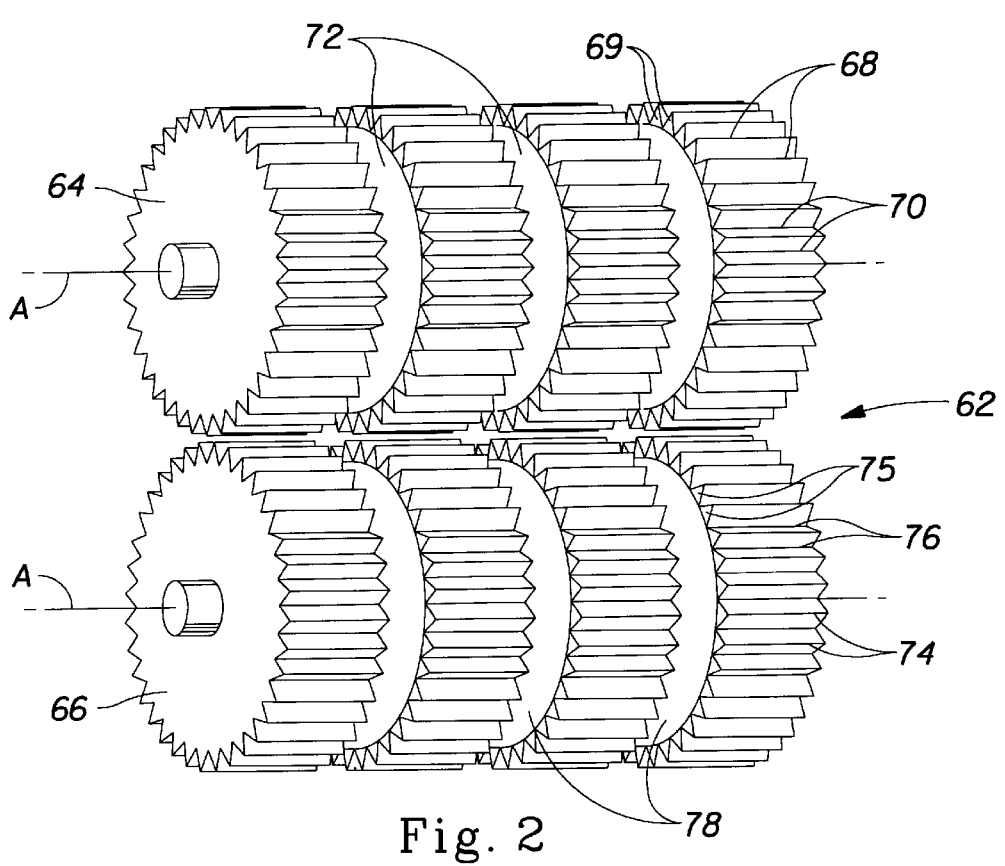
FIG. 2 is a simplified perspective view of another portion of an apparatus that could be used to carry out the method of the present invention.
Figure 3:
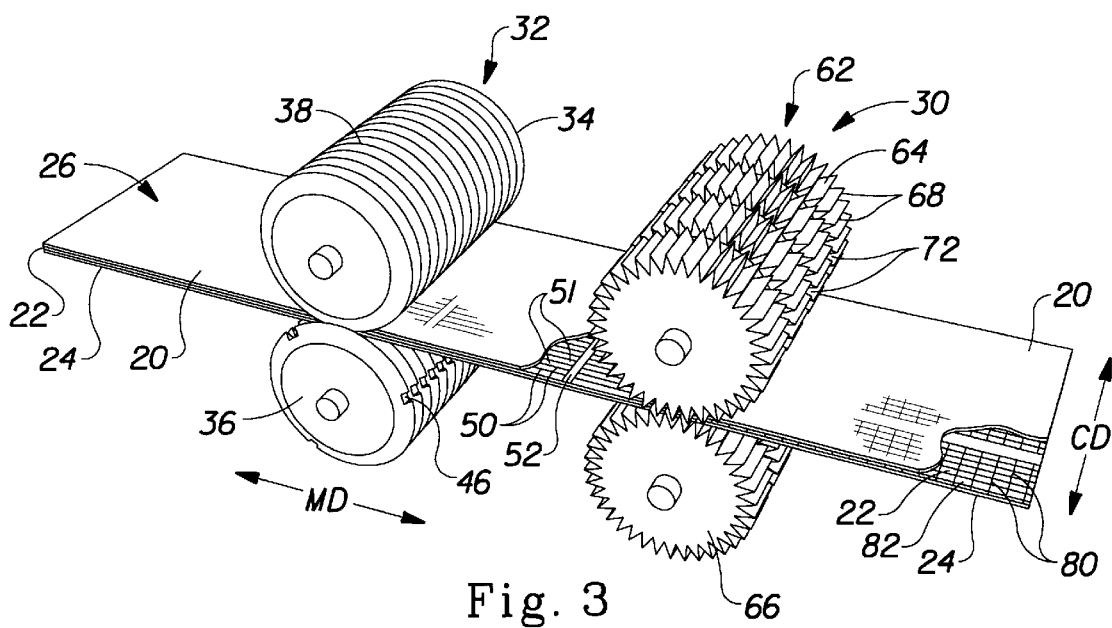
FIG. 3 is a simplified perspective view of a composite web of material passing through the apparatus shown in FIG. 1 and the apparatus shown in FIG. 2, with the composite web being shown partially fragmented.

FIGS. 1 and 2 show two portions of a preferred embodiment of an apparatus 30 (shown in FIG. 3) that can be used to carry out the method of making a particulate material of the present invention, and more specifically which can be used to prepare a particulate absorbent material. FIG. 3 is a simplified perspective view of a composite web of material 26 passing through the portions of the apparatus shown in FIG. 1 and FIG. 2 in sequence. The process shown in FIG. 3 is especially preferred if: it is desired to form regular slits or particles; it is desired to provide the carrier web with a degree or extensibility; and/or it is desired to provide the carrier web with an added degree of softness, flexibility, or both.

It should be understood that the method of the present invention is shown and described in terms of a method for making particulate material. The making of a slitted material is an intermediate step in the method of making particulate material. To make a slitted material, it is only necessary to cut the web of absorbent material so that it is provided with slits that are oriented in one direction. The slits can be oriented in the longitudinal direction, the transverse direction, or at an angle to the longitudinal and transverse directions. To make particulate material, the web of absorbent material is slit in more than one direction (for example, the web can be slit twice with slits oriented perpendicularly to each other). In other embodiments of making particulate material, the web of absorbent material may be provided with slits that are oriented at an angle to each other that is not perpendicular (e.g., to form a diamond-shaped pattern). The slits may be linear, curvilinear, or they may have some linear segments and some curvilinear segments.

As shown in FIG. 3, one embodiment of the method of making a particulate material according to the present invention preferably comprises: (a) providing a carrier material, which in this case is in the form of a web and is referred to as a first web (or "carrier web") 20 having a first yield to break point under tensile forces; (b) providing a destructible material for forming into particulate material, which in this case is referred to as a second material and is in the form of a web of material (second web of material) 22 on the carrier web 20 to form a composite web 26, which second web of material 22 has a second yield to break point under tensile forces that is lower than the yield to break point of the carrier web 20; (c) providing an apparatus 30 for mechanically straining the composite web 26, the apparatus having an element with at least one patterned surface thereon; and (d) subjecting the composite web 26 to a mechanical straining process using the apparatus 30 by impressing the patterned surface into the composite web 26 so that the second web of material 22 is at least partially formed into particulate material without forming the carrier web 20 into particulate material.

In the embodiment shown, the carrier web 20 can comprise any suitable material having a yield to break point under tensile forces that is greater than that of the second web of material 22. The carrier web 20 may be manufactured from a wide range of materials such as woven and nonwoven materials; polymeric materials such as apertured formed thermoplastic films, apertured or unapertured plastic films, and hydroformed thermoplastic films; porous foams; polyurethane foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers); bicomponent fibers (that is, fibers having a core of one material which is enclosed in a sheath made of another material); or from a combination of natural and synthetic fibers.

Preferably, the carrier web 20 comprises a material that is also suitable for containing the particulate material that will be formed, and retaining the same in its desired position inside the absorbent article. For example, the carrier web 20 can serve such as a cover or topsheet, or as a backsheet for the absorbent article. Preferably, if the carrier web 20 is used for containing the absorbent material, any pores or openings in the carrier web 20 are smaller than the chopped particles for containment of those particles within the absorbent article.

Suitable apertured films for use as a carrier web 20 are described in U.S. Pat. No. 3,929,135, issued to Thompson on Dec. 30, 1975; U.S. Pat. No. 4,324,246, issued to Mullane, et al. on Apr. 13, 1982; U.S. Pat. No. 4,342,314, issued to Radel, et al. on Aug. 3, 1982; U.S. Pat. No. 4,463,045, issued to Ahr, et al. on Jul. 31, 1984; and U.S. Pat. No. 5,006,394, issued to Baird on Apr. 9, 1991. One especially preferred apertured film carrier web useful as an outer cover for the absorbent material comprises a formed film described in one or more of the above patents and marketed on sanitary napkins by The Procter & Gamble Company of Cincinnati, Ohio as the "DRI-WEAVE" topsheet.

In the preferred embodiment of the process shown in the drawings, however, the carrier web 20 comprises a nonwoven web. A number of different types of nonwoven webs are suitable for use as the carrier web 20. Suitable nonwoven webs can include, but are not limited to: carded nonwovens; spunlaced nonwovens; needle punched nonwovens; spunbonded nonwovens; air laid nonwovens, including thermally bonded air laid nonwoven webs, latex bonded air laid nonwoven webs, and multi-bonded air laid nonwoven webs; and thermally bonded wet laid nonwoven webs.

One particularly preferred spunbonded nonwoven material is a 19 g/yd$^2$ (22.5 g/m$^2$) spunbonded polypropylene nonwoven material referred to as product No. 065MLPV60U (or "P-9") obtained from Fiberweb, North America of Washougal, Wash. Another particularly preferred nonwoven material is a spunbonded polyethylene nonwoven material known as COROLIND sold by Corovin GmbH, Peine, Germany which can be obtained in two basis weights, 23 gsm and 30 gsm.

Suitable thermally bonded air laid material (which may be referred to as "TBAL" for brevity) for use as a carrier web 20 can be fabricated from a blend of cellulose and synthetic fibers. Preferred thermally bonded air laid materials are described in U.S. Pat. No. 5,607,414 entitled "Catamenial Absorbent Structures Having Thermally Bonded Layers For Improved Handling of Menstrual Fluids, and Their Use in Sanitary Napkins Having Improved Fit and Comfort" issued to Richards, et al. on Mar. 4, 1997.

A suitable low density latex bonded air laid material (which may be referred to as "LBAL" for brevity) for use as a carrier web 20 is a material having a basis weight of about 80 g/m$^2$ known as product No. F6413MHB, which is obtained from Walkisoft, USA of Mt. Holly, N.C.

A suitable multi-bonded air laid nonwoven material (which may be referred to as "MBAL" for brevity) comprises about 77% cellulose fibers, about 20% powder binder, and about 3% latex binder (1.5% sprayed on each side of the web) and has a basis weight of about 50 g/yd$^2$ (about 60 g/m$^2$). (Unless otherwise stated, all percentages herein are by weight.) Such a multi-bonded air laid nonwoven is preferably obtained as product No. 90830X312 from Merfin Hygienic Products, Ltd. of Delta, British Columbia, Canada.

Suitable thermally bonded wet laid nonwoven webs (which may be referred to as "TBOWL" for brevity) are described in U.S. Pat. No. 5,549,589 entitled "Fluid Distribution Member for Absorbent Articles Exhibiting High Suction and High Capacity" issued to Horney, et al. on Aug. 27, 1996.

The carrier web 20 may also comprise a material that is extensible, or stretchable prior to any mechanical manipulation thereof, if desired. For example, a carrier web could comprise an apertured film made of a polyethylene/Kraton blend such as the Exxon film formerly known as EXX-7, available from the Exxon Corporation. Additional extensible materials that are suitable for use as the carrier web 20 are described in U.S. Pat. No. 5,611,790 issued to Osborn.

Preferably, at least one carrier web is used in the method of the present invention. In some embodiments of the method, a single carrier web will be placed adjacent to one side of the web of material that will be slit or formed into particulate material (the "second web of material" 22). As shown in FIG. 3, in other embodiments of the present invention, two or more carrier webs may be used. If two or more carrier webs are used, at least one carrier web, first carrier web 20, will be placed adjacent to one side (the first side or surface) of the second web of material 22. A second carrier web, carrier web 24, will be placed adjacent to the other side (the second side or surface) of the second web of material 22 that will be slit or formed into particulate material. Placing a carrier web adjacent to each side of the second web of material 22 is particularly preferred when forming a particulate material so that when the particulate material is formed, it will be contained between the two carrier webs 20 and 24.

The second web of material 22 (the web of material that will be slit or formed into particles) should have certain characteristics. The second web of material 22 should have a second breaking point that is lower than the breaking point of at least one of the carrier web(s). The second web of material 22 should preferably be capable of being readily cut, preferably into strips and/or particles. The second web of material 22 preferably has a second yield to break point under tensile forces that is lower than the yield to break point of both of the carrier webs 20 and 24. In other words, the second web of material 22 is more easily destructible (for example, more easily cut or broken) than the carrier webs 20 and 24.

In the preferred embodiment of the process, the second web of material 22 comprises a web of absorbent material. Some suitable absorbent materials for use as the second web of material 22 comprise: certain nonwoven materials, including but not limited to, tissue webs, any of the types of air laid webs of absorbent material specified as being suitable for use as a carrier web; porous, absorbent, polymeric macrostructures comprising interparticle crosslinked aggregate; absorbent sponges, absorbent foams; and any other type of absorbent material that has the characteristics described herein. Suitable porous, absorbent, polymeric macrostructures comprising interparticle crosslinked aggregate are described in the following patents: U.S. Pat. No. 5,124,188, issued to Roe, et al. on Jun. 23, 1992; U.S. Pat. No. 5,180,622 issued to Berg, et al. on Jan. 19, 1993; and U.S. Pat. No. 5,330,822 issued to Berg, et al. on Jul. 19, 1994.

In the preferred embodiment of the present invention shown in the drawings, the second web of material 22 is an absorbent foam material. Suitable absorbent foams for the second web of material 22 are described in U.S. Pat. No. 5,260,345 issued to DesMarais, et al. on Nov. 9, 1993; U.S. Pat. No. 5,268,224 issued to DesMarais, et al. on Dec. 7, 1993; U.S. Pat. No. 5,387,207 issued to Dyer, et al. on Feb. 7, 1995; U.S. Pat. No. 5,550,167 issued to DesMarais on Aug. 27, 1996; U.S. Pat. No. 5,563,179 issued to Stone, et al. on Oct. 8, 1996; U.S. Pat. No. 5,650,222 issued to DesMarais, et al. on Jul. 22, 1997; and allowed U.S. patent application Ser. No. 08/542,497 filed Oct. 13, 1995, by Dyer, et al. (P&G Case 5546R). Such absorbent foam materials are particularly preferred because they can be provided with good resistance to compression and resiliency following compression. The absorbent foam materials described in these different patents have properties that allow them to acquire and/or store various bodily exudates. They may also be provided with the ability to absorb particular types of bodily exudates (e.g., menses, runny bowel movements, and/or urine).

It is noted that some of the same materials are described as being suitable for use as both a carrier web and as the second web of material. It should be understood, however, that while the specified materials can be used as either component of the composite web, the materials used in the composite web 26 should be chosen so that there is a difference in the breaking points between the materials used as the different components of the composite web. Thus, the same material would typically not be chosen for use both as the carrier web and as the second web of material. For instance, if a thermally bonded air laid material is chosen for use as the carrier web, then a material with a lower breaking point, such as an absorbent foam material, should be chosen as the second web of material, rather than another thermally bonded air laid material. There are exceptions to this, however, as discussed in greater detail in the portion of this specification describing alternative embodiments. For instance, the same materials could be used if one of them is treated to reduce its breaking point.

The web of absorbent material 22 can be of any thickness that is capable of passing through the nip between the two sets of rolls. The thickness of the absorbent foam materials described herein is preferably between about 1 mm and about 5 mm, and more preferably is between about 1.5 mm and about 2.5 mm. However, in other embodiments of the method of the present invention (particularly where the apparatus comprises mating plates), lesser or greater thicknesses can be used.

The web of absorbent material 22 has two surfaces, a first surface and a second surface. The surfaces of the web of absorbent material 22 are preferably substantially planar, although providing an absorbent material with non-planar surfaces is also possible. The web of absorbent material 22 and the carrier webs 20 and 24 are preferably arranged as a laminate to form the composite web 26. The carrier webs 20 and 24 are preferably slightly larger in their cross-machine direction ("CD" in FIG. 3) dimension so that they extend beyond the edges of the web of absorbent material 22. The extensions of the carrier webs 20 and 24 beyond the longitudinal edges of the web of absorbent material 22 are preferably joined together, such as by adhesives, so that a seal will be formed along the longitudinal edges of the composite web 26 to contain the absorbent material after it is formed into particles. The term "joined", as used herein, encompasses configurations in which an element is directly secured to another element by affixing the element directly to the other element; configurations in which the element is indirectly secured to the other element by affixing the element to intermediate member(s) which in turn are affixed to the other element; and configurations in which one element is integral with another element; i.e., one element is essentially part of the other element.

The remainder of the carrier webs 20 and 24 can simply be placed adjacent to the surfaces of the web of absorbent material 22. If a particulate material is being formed, the web of absorbent 22 need only be placed between the carrier webs 20 and 24 and need not be joined thereto. Alternatively, the carrier webs may also be joined to the surfaces of the web of absorbent material 22. If it is desirable to join one or more of the carrier webs to the web of absorbent material 22, adhesive may be applied between one of the carrier webs and the web of absorbent material 22, or between the web of absorbent material 22 and both of the carrier webs. The carrier webs 20 and 24 can be joined to the web of absorbent material 22 by attachment means such as those well known in the art. For example, these components of the composite web 26 may be secured together by a uniform continuous layer of adhesive, a patterned layer of adhesive, or an array of separate lines, spirals, or spots of adhesive between the web of absorbent material and the carrier webs. Adhesives which have been found to be satisfactory are manufactured by H.B. Fuller Company of St. Paul, Minn. under the designation HL-1258 or H-2031.

If these components are joined together, this is preferably accomplished by an open pattern network of filaments of adhesive as is disclosed in U.S. Pat. No. 4,573,986 entitled "Disposable Waste-Containment Garment", which issued to Minetola, et al. on Mar. 4, 1986. An example of an open pattern network of filaments comprises several lines of adhesive filaments swirled into a spiral pattern such as illustrated by the apparatus and method shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Alternatively, these components can be joined by heat bonds, pressure bonds, ultrasonic bonds, dynamic mechanical bonds, or any other suitable attachment means or combinations of attachment means that are known in the art.

Although some of the absorbent materials described herein (such as the absorbent foam materials) are incompatible with conventional bonding techniques, if the edges of the composite web 26 are sealed as described above, and the composite web is not excessively stressed, such bonding is sufficient for the purposes described herein.

FIGS. 1 and 2 show two portions of an apparatus that is used to mechanically strain the composite web of material 26 in a particularly preferred embodiment of the method of the present invention. The arrangement of these portions into the overall apparatus 30 is shown in FIG. 3. The apparatus 30 preferably comprises an element or component that has at least one patterned surface thereon. In the preferred embodiment shown in FIGS. 1–3, the apparatus 30 is provided with several components having patterned surfaces thereon.

The portion of the apparatus shown in FIG. 1 comprises a first pair or set of cylindrical rollers (or rolls) 32. The first pair of rolls 32 comprises a top roll 34 and a bottom roll 36. The rolls 32 and 34 have spaced axes, A. Each of the rolls has a pattern on its surface. In FIG. 1, the top roll 34 has a plurality of ridges 38 and valleys 40 that are disposed around the circumference of the cylindrical roll 34. The ridges 38 form a plurality of triangular-shaped teeth 39 on the surface of the top roll 34. Preferably, as shown in greater detail in FIG. 2A, the teeth 39 have cross-sections in the form of isosceles triangles. The apex of the teeth 39 may be slightly rounded, if desired.

The teeth 39 on the top roll 34 can be of any suitable size and pitch. The term "pitch", as used herein, refers to the distance between the apexes of adjacent teeth. In the preferred embodiment shown in the drawings, the depth (or height) of the teeth is preferably between about 0.1 inches and about 0.17 inches (about 2.5 mm to about 4.3 mm). The pitch is preferably between about 1 mm and about 5 mm, and more preferably is between about 1.5 mm and about 2.5 mm. The pitch of the teeth establishes the width of strips into which the absorbent material is cut or chopped.

The bottom roll 36 in the first pair of rolls shown in FIG. 1 also comprises a plurality of ridges 42 and valleys 44 that are disposed around its circumference. The ridges form a plurality of triangular-shaped teeth 43 on the surface of the bottom roll 36. The teeth 43 on the bottom roll 36 preferably also have cross-sections in the form of isosceles triangles. The teeth 43 on the bottom roll 36 preferably are of the same size as those on the top roll. The bottom roll 36 preferably also comprises several evenly-spaced thin planar channels 46 on the surface of the bottom roll 36 that are oriented parallel to the axis, A, of the bottom roll. In this embodiment, the spaced apart channels 46 in the bottom roll 36 preferably have a width of 2 mm. The "length" of the teeth 43 in the bottom roll 36 measured around the circumference of the bottom roll between the spaced apart channels is 8 mm. A suitable patterned roll for use as the bottom roll is described in U.S. Pat. No. 5,518,801 entitled "Web Materials Exhibiting Elastic-Like Behavior" issued to Chappell, et al. on May 21, 1996.

The triangularly-shaped teeth 39 in the top roll 34 preferably are offset from the teeth 43 on the bottom roll 36. The offset is such that the triangularly-shaped teeth 39 in the top roll 34 align with the valleys 44 on the bottom roll 36. That is, the teeth in the top roll 34 are centered relative to the valleys 44 on the bottom roll 36, and could intermesh (or "engage") the portions of the bottom roll 36 that define the valleys 44 on the bottom roll 36. In this embodiment, however, rolls are preferably spaced so that the triangularly-shaped teeth 39 in the top roll 34 only partially engage with the valleys 44 on the bottom roll 36. The rolls 34 and 36 are preferably driven in opposite directions.

In a preferred embodiment, the triangularly-shaped teeth 39 in the top roll 34 and the valleys 44 on the bottom roll 36 should be spaced so that they are partially intermeshing. The degree to which the teeth on the opposing rolls intermesh is referred to herein as the "engagement" of the teeth. The engagement of the teeth is represented by reference letter E in FIG. 2A. The engagement, E, is the distance between a position designated by plane $P_1$ where the apexes of the teeth on the respective rolls are in the same plane (0% engagement) to a position designated by plane $P_2$ where the apexes of the teeth of one roll extend inward beyond the plane $P_1$ toward the valleys on the opposing roll. The engagement of the teeth can be expressed as a percentage of the pitch (distance between the apexes of the teeth on one of the rolls), or in terms of a measured distance. Since the height of the teeth may be greater than the pitch, the engagement may be a value that is greater than 100% (for instance, if the engagement is greater than the pitch). Preferably, the engagement is between about 15% and about 120% of the pitch length, and more preferably is between about 65% and about 100% of the pitch length. The engagement expressed in terms of a measured distance is preferably between about 0.01 inch to about 0.07 inch (about 0.25 mm to about 1.8 mm), and more preferably is between about 0.04 inch to about 0.06 inch (about 1 mm to about 1.5 mm).

Figure 2A:
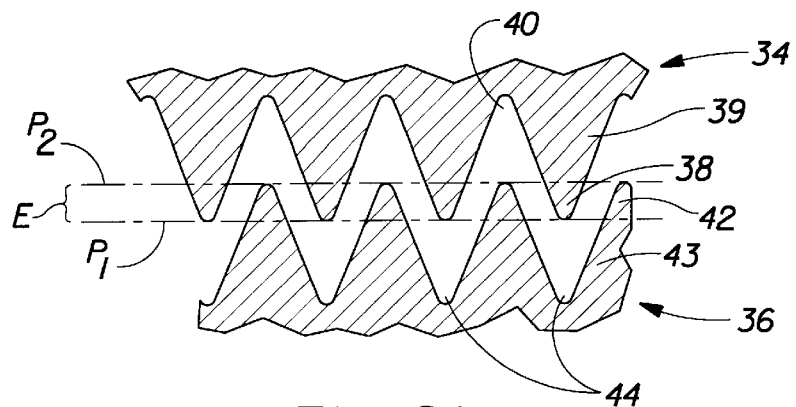
FIG. 2A is a fragmented cross-sectional view taken of the nip between the rolls shown in FIG. 1 showing the teeth of the rolls being partially engaged.

In other embodiments, however, the teeth 39 in the top roll 34 need not be aligned with the valleys 44 in the bottom roll 36 as shown in FIG. 2A. That is, the teeth 39 may be out of phase with the valleys 44. The teeth 39 may be out of phase to any suitable degree relative to the valleys 44 in the bottom roll 36. The teeth 39 may range from being offset slightly from direct alignment relative to the valleys 44 on the bottom roll 36 to being completely offset so that there could be no intermeshing of the teeth of one roll with the valleys of the other. For example, instead of the teeth of one roll being aligned with the valleys on another roll, the teeth of one roll could be directly aligned with the teeth of the other roll. Any of these arrangements can be used to apply a sufficiently high concentrated force to the absorbent material to cause a localized failure of the same.

The method of the present invention is carried out by feeding the composite web 26 between the mating rolls. As shown in FIG. 3, the composite web 26 is fed in a machine direction (MD) into the nip between the rolls 34 and 36. The carrier webs 20 and 24 face the patterned surfaces on the rolls. The least destructable web(s) (the carrier webs 20 and 24) should face the patterned rolls for ease in removing the mechanically strained composite web 26 from the patterned rolls. The rolls subject the composite web 26 to a mechanical straining process by impressing the patterned surface into the composite web 26 with a force that is greater than the second yield to break point, but less than the first yield to break point. This results in the web of absorbent material 22 being at least partially slit without slitting the carrier webs 20 and 24.

FIG. 3 shows the condition of the composite web 26 after it passes through the nip between the first pair of rolls 32. As shown in FIG. 3, the top and bottom carrier webs 20 and 24 have a pattern of corrugations formed therein that corresponds to the combination of the patterns on the adjacent rolls, 34 and 36. The carrier webs 20 and 24, however, are not slit or cut. The intermediate web of absorbent material 22 has a plurality of slits 50 formed therein. The slits 50 are oriented in the machine direction. The slits are intermittent and separated by cross-machine direction bands of unslit material 52. This is due to the presence of the channels 46 on the bottom roll 36. Between the slits 50, the surfaces of the web of absorbent material 22 may remain substantially planar.

The web of absorbent material 22 is slit while the carrier webs 20 and 24 are not slit because the web of absorbent material has a lower yield to break point under tensile forces (the forces exerted by the straining process) than the carrier webs 20 and 24. In other words, the outer carrier webs 20 and 24 can withstand a higher rate of strain than the absorbent material 22 which results in a completely or partially disintegrated absorbent material fully contained between two layers of material.

The web of absorbent material 22 need not have bands of unslit material 52 therein. In other embodiments, continuous slits can be formed in the web of absorbent material 22. Continuous slits 50 will be formed if the bottom roll 36 is modified by replacing the channels 46 therein with sections that form continuous ridges and valleys. In such an embodiment, the bottom roll 36 will be identical to the top roll 34.

If the slits 50 are continuous, the web of absorbent material 22 will be formed into a plurality of disconnected strips 51 that have been separated by the slitting process. These may be referred to as "strands" herein, although they are not comprised of wound fibers or the like. These strips or strands 51 can be very narrow, or they can be fairly wide with widths increasing up to slightly less than the width of the web (depending on the apparatus used).

If these strips 51 are very narrow, they may resemble spaghetti noodles in the overall dimensions. However, the sides of these strips would typically be flat, rather than rounded. The width of the strips 51 depends on the pitch of the teeth on the rolls. Thus, some non-limiting dimensions of the strips 51 in the preferred embodiment shown might range from about 1 mm to about 5 mm wide, and are preferably between about 1.5 mm and about 2.5 mm wide. The strips 51 can be any suitable length. They can range from lengths that are slightly greater than their width dimension, to an infinite length. Typically, their maximum length will be limited by the length of the product into which they are incorporated.

If the slits 50 are intermittent, the web of absorbent material 22 will be formed into a plurality of connected strips 51. The slits 50 can be of any suitable length so that the strips 51 are connected in any suitable manner. It may, for example, be desirable to have the strips 51 remain connected at their ends and/or at their middle portions for ease in handling them in the manufacturing process. The connection of the strips 51 may eliminate the need for a carrier web in the step of passing the web of absorbent material 22 into the nip between the first set of rolls. It should also be understood that in situations where the strips 51 are continuous, there also may be no need for either carrier web in the step of passing the web of absorbent material 22 into the nip between the first set of rolls since tension will be placed on the absorbent material in the machine direction, and this will support the absorbent material without a carrier web or webs even after slitting.

The web of absorbent material 22 can be provided with slits 50 that are in any suitable configuration (depending on the apparatus used). The slits 50 can be linear, curvilinear, or they can be comprised of some linear segments and some curvilinear segments.

The method of the present invention is also not limited to forming slits that are oriented only in the machine direction. In other embodiments, the first pair of rolls 32 can be configured similarly to the second pair of rolls 62 (which is described in greater detail below). In such a case, the slits formed in the web of absorbent material will be oriented in the cross-machine direction (or "CD"). In still other embodiments, either pair of rolls can be oriented on a bias (that is, at an angle) relative to the machine direction to provide slits that are diagonally-oriented. If it is desired to make a slitted absorbent material according to the method of the present invention, the process will be complete after the composite web 26 passes between the first pair of rolls 32. If it is desired to form particulate material, then the steps described below will be performed.

At this point in the process, (between the first and second sets of rolls 32 and 62) it is possible to perform additional operations on the composite web 26. For example, an additional web of material, such as a continuous web of apertured film topsheet material, could be joined to the composite web 26 between the first and second sets of rolls. Alternatively, such an additional material could be cut into individual pieces and joined to the composite web 26 between the first and second sets of rolls.

The second pair or set of rolls 62 is shown in greater detail in FIG. 2. The second set of rolls 62 also comprises top and bottom rolls, top roll 64 and bottom roll 66. Each of these rolls has a pattern on its surface. As shown in FIG. 2, the top roll 64 has a plurality of ridges 68 and valleys 70 that run parallel to the axis, A, of the top roll 64. The ridges 68 form a plurality of triangular-shaped teeth 69 on the surface of the top roll 64. The top roll 64 may also have a plurality of spaced apart channels 72 that are oriented around the circumference of the cylindrical roll.

The bottom roll 66 in the second pair of rolls shown in FIG. 2 has a pattern that is identical to that of the top roll 64 in the second pair of rolls. The bottom roll 66 has a plurality of ridges 74 and valleys 76 that run parallel to the axis, A, of the bottom roll 66. The ridges 74 form a plurality of triangular-shaped teeth 75 on the surface of the bottom roll 66. The bottom roll 66 may also have a plurality of spaced apart channels 78 that are oriented around the circumference of the cylindrical roll. A suitable set of rolls for use as the second set of rolls is described in U.S. Pat. No. 5,518,801 issued to Chappell, et al.

In the preferred embodiment shown in the drawings, the top and bottom rolls 64 and 66 in the second set of rolls 62 have teeth and ridges and valleys having similar characteristics to those elements of the first set of rolls. Thus, the teeth are preferably in the shape of isosceles triangles. The teeth preferably also have the same pitch. However, in other embodiments, the pitch of the teeth on the second set of rolls 62 can be less or greater than the pitch of the teeth on the first set of rolls 32. In the preferred embodiment shown, the spaced apart channels 72 and 78 in the second set of rolls preferably have a width of 2 mm. The "length" of the teeth measured transversely across the rolls (parallel to the axes, A) between the spaced apart channels 72 and 78 on the surface of each roll is 8 mm. The triangular-shaped teeth on the top and bottom rolls preferably also have the same engagement as the teeth on the first set of rolls, although the engagement can be varied as well. The top and bottom rolls are preferably rotating in opposite directions. The composite web 26 is similarly fed into the nip between the rolls 64 and 66.

FIG. 3 shows that when the composite web 26 leaves the nip between the second set of rolls 62, at least a portion of the absorbent material 22 is further provided with a plurality of slits 80 that are oriented in the cross-machine direction. This causes the absorbent material 22 to be formed or chopped into a plurality of particles 82. In the preferred embodiment shown in the drawings, the particles 82 have a square surface area that is about 1.5 mm×1.5 mm. The particles 82 are preferably about 2 mm thick (the thickness of the absorbent foam material).

In some embodiments, the particles of absorbent material 82 can be connected to unslit strips that are left in the absorbent material. In other embodiments, continuous cross-machine direction (CD) slits can be formed in the web of absorbent material 22 if the top and bottom rolls are modified by replacing the channels, 72 and 78, thereon with sections that form continuous ridges and valleys. Again, the carrier webs 20 and 24 are not slit, but have another pattern formed therein. The overall pattern formed in the carrier webs 20 and 24 resembles a grid with a combination of the impressions created by first and second sets of rolls 32 and 62.

In other embodiments, if it is desired to form the entire web of absorbent material 22 into particulate material, both sets of rolls can be modified by replacing any channels thereon with sections that form continuous ridges and valleys. This will result in the formation of continuous machine direction slits, and then continuous cross-machine direction slits which intersect to form a plurality of chopped particles. The particles may be of any suitable size. The particles preferably have a largest dimension having a nominal size, that is preferably between about 1.0 mm and about 25.4 mm, and more preferably between about 2 mm and about 16 mm. However, particles as small as 0.5 mm and smaller, and particles larger than about 25.4 mm are contemplated. Particles having a nominal size of about 1.0 mm or greater are those which are generally retained on the surface of a U.S. Standard No. 18 mesh sieve screen. Particles having a nominal size of less than about 25.4 mm are those which generally pass through a U.S. Standard 25.4 mm sieve screen.

The chopped particles can be of any suitable shape. They may have regular shapes or irregular shapes. Examples of particles having regular shapes are particles in the shape of cubes, three dimensional rectangular particles, prisms, or other parallelepipeds. In still other embodiments, as will be described in greater detail below, the pattern on the surfaces of the rolls can be varied to provide a virtually unlimited number of variations of slits or particle shapes in the web of absorbent material 22. The particles can be all of the same general size and/or shape, or they can be of varying sizes and/or shapes.

In one preferred embodiment, the particles of absorbent foam material are generally in the configuration of parallelepipeds. When the particles of absorbent foam material are described as being "generally" in a particular configuration, it is understood that they need not be exactly in the configuration specified, and that all of the particles need not be exactly in the configuration specified. It is sufficient if some of the particles are roughly in the shape specified so that they are recognizable as having such a shape.

The particulate absorbent material 82 formed by the method described above is trapped and contained between the two carrier webs 20 and 24. The composite web, thus, forms a self-contained structure comprising particulate absorbent material. The composite web 26 with the particulate absorbent material 82 therein can then be incorporated into individual absorbent articles. (Of course, in embodiments in which the absorbent material is not formed into particles, but is only slit, the self-contained structure will comprise slit absorbent material, rather than particles.) The composite web 26 can be incorporated into absorbent articles in its flat condition as it leaves the nip between the second set of rolls. In other embodiments, the composite web can be folded or otherwise manipulated into the desired shape for inclusion in an absorbent article.

The present invention provides an improved method of making and providing a self-contained slitted or particulate absorbent material for absorbent articles. The method of the present invention involves very few steps and significantly less additional equipment, and does not require a delivery system that uses compressed air or a closed receptacle for containing the particulate material. In addition, because the particles are placed in a laminate structure, and are not blown or transferred from a delivery system, the result is a significant improvement in the control of the particle distribution. That is, the particles can be placed in precise locations within an absorbent article. The method of the present invention also eliminates the need to re-meter the quantity of the particulate material delivered to the absorbent article.

The method of the present invention also provides the ability to maintain the characteristics of more than one layer of absorbent material relative to the other layers. For example, there could be two (or more) layers of absorbent material, such as absorbent foam, with different characteristics (e.g., pore size, hydrophilicity, etc.). For instance, the uppermost foam layer may have a larger pore size than the lower foam layer(s) to establish a capillary gradient from the top of the absorbent article to the bottom of the absorbent article. The method of the present invention is capable of forming one or more of these layers of foam material into strips or particulate material while maintaining the strips of particles of foam in their original orientation. This preserves the desired relationship, unlike prior processes which involved air delivery systems. The prior processes would provide a random mixture of these particles instead.

In addition, the method of the present invention provides numerous other advantages. The method of the present invention can be used to provide the carrier web(s) with a degree of extensibility due to the formation of a strainable network of regions therein by the patterned rolls. The formation of a strainable network region in a material to provide the same with extensibility is discussed in greater detail in the Chappell, et al. patent. The method of the present invention can also be used to provide the carrier web(s) with added softness due to the impression of the patterned surfaces therein. This provides advantages similar to those associated with embossing processes. The method of the present invention can also be used to provide the carrier web(s) with increased flexibility due to the plurality of additional bending axes imparted into the carrier web(s) by the ridges and valleys on the patterned rolls. Further, as described in greater detail below, the method of the present invention may also provide the advantage of improving the integrity between the layers of the composite web.

The preferred embodiment of the method of the present invention also provides advantages over impression-related slitting methods (that is, methods of slitting materials against a rigid backing or other methods of puncturing). The embodiment of the method of the present invention described above is particularly preferred because it employs a strain-related type of slitting. Impression-related slitting methods suffer from several drawbacks. The cutting blade will have a high tendency to wear out, particularly if there is metal-to-metal contact between the cutting blade and the backing surface. Another disadvantage is that there are limitations to the location of an impression-related slitting operation in the process of making an absorbent article. It is not possible to slit an intermediate web in a composite web using an impression-related slitting method. It is also difficult to form the narrow spaghetti-like strips of material and small particles that the method of the present invention is capable of providing using impression-related slitting methods.

In addition it is generally difficult to slit a web of material after it is combined with another web of material without slitting both materials using impression-related slitting methods. While it is possible to slit only one web of such a combined web, great care has to be taken in setting the distance between the cutting blade and the backing surface so that only one of the webs is slit. Even after taking such care to set the cutting blade, it would be difficult to slit completely through the web of material without slitting the adjacent material. The method of the present invention, on the other hand, is well suited to slitting completely through one material without slitting the other. It should be understood, however, that the method of the present invention is not limited to one in which the destructible material is completely slit or broken. The method of the present invention also includes embodiments in which the destructible material merely fractures.

Numerous alternative embodiments of the method of the present invention are possible. Several of these show even further advantages of the method of the present invention. A non-limiting number of such embodiments are described below.

In alternative embodiments, the material that is slit or formed into particulate material may be in forms other than a web. The material that is slit or formed into particulate material (the destructible material) may be in any suitable form, including but not limited to, a piece, one or more strips, a block, one or more layers, a laminate, or a web. The material that is described above as being the carrier web may also be in forms other than a web. The carrier material may be in any of the forms that are described above as being suitable for the material that is slit or formed into particulate material. In some cases, the carrier material can be omitted altogether. In addition, it should be understood that these two components, the carrier material and the destructible material, may be in different forms from each other. For example, the carrier material may be in the form of a continuous web, and the destructible material may be in the form of a piece, one or more layers, one or more strips, or a laminate.

In those alternative embodiments in which the destructible material comprises one or more layers, or a laminate, the different layers thereof may be fractured to differing extents or in different patterns. Numerous such embodiments are possible. For example, the destructible material may comprise two layers of absorbent material. One of the layers of absorbent material, such as the layer that will be positioned in the portion of the absorbent article that is worn closest to the wearer's body, can be slit or formed into particulate material to provide improved acquisition and/or softness. The underlying layer could be left without slitting it or forming it into particulate form. Alternatively, one of the layers such as the top layer could be formed into particulate material, and the other layer, such as the underlying layer could be slit so that it is formed into strips.

One method that can be used to fracture layers to differing extents or in different patterns is to provide one or more of the layers with weakened areas to facilitate the fracturing or slitting. The material to be fractured or slit can be weakened in the desired regions by applying localized force to those regions of the material. For example, the material in issue could have a pattern of weakened regions formed therein by impressing a pattern from a bonding apparatus into the surface of the material to be fractured or slitted prior to incorporating that material into a composite web.

In other embodiments, it may be desirable to slit or partially slit at least one of the carrier webs. For example, when the material that is to be slit or formed into particulate material comprises an absorbent foam and the carrier material comprises a nonwoven web, it may be desirable to form slits in the nonwoven carrier web that covers the body-facing side of the absorbent foam material. The slitting can, thus, be used to form an apertured topsheet. The slits can also allow at least some portions of the particles or strips of the absorbent foam material to be exposed to aid in the acquisition of liquids. Stretching and/or folding the composite web into a convex configuration may be used to aid in opening the slits. These slits will typically be oriented in similar direction(s) to the slits formed in the absorbent material. Preferably, the slits in the carrier web are intermittent so that the carrier web(s) will retain a degree of integrity.

In embodiments in which the destructible material comprises more than one layer, different types of absorbent material (such as foam material) could be used for each of the layers. For example, the layer of absorbent foam material that will be positioned closest to the wearer's body can comprise a soft foam with large cells for improved acquisition and comfort. The underlying layer could comprise a foam that is more firm, and which has smaller cells to establish a capillary gradient to wick liquids away from the foam having the larger cells for storage.

In alternative embodiments of the method of the present invention, the positions of the top and bottom rolls of the pairs of rolls can be reversed. In these or other alternative embodiments, the order of the pairs of rolls could be changed so that the composite web 26 passes through the second pair of rolls before it passes through the first pair of rolls.

Figure 3A:
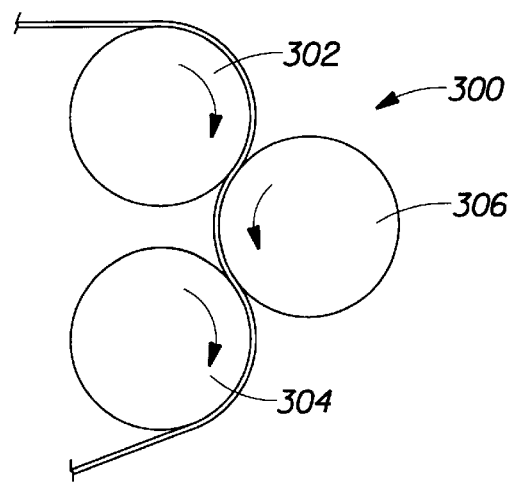
FIG. 3A is a schematic side view of an alternative apparatus for making particulate material according to the present invention.

As shown in FIG. 3A, in still other alternative embodiments, the two pairs of rolls shown in FIG. 3 could be replaced by an apparatus 300 comprising a combination of three rolls that is capable of chopping the absorbent material into particles. The three roll combination preferably comprises a pair of rolls comprising rolls 302 and 304, both of which have a pattern thereon. One of the patterned rolls, for example first roll 302, has a plurality of grooves that define teeth that are oriented in the machine direction. This roll can be similar to the rolls in the first set of rolls 32 shown in FIG. 3. The other patterned roll, second roll 304, has a plurality of grooves that define teeth that are oriented in the cross-machine direction. This roll can be similar to the rolls in the second set of rolls 62 shown in FIG. 3. Both patterned rolls preferably have hard surfaces, such as steel.

The two patterned rolls 302 and 304 operate in conjunction with a third roll, roll 306 which has a compressible and resilient surface (e.g. rubber). The third roll 306 forms a pressure biased nip with each of the patterned rolls 302 and 304. In this embodiment, the patterned rolls do not even need to partially engage with each other. As shown in FIG. 3A, instead of being fed through a nip between the two patterned rolls, the composite web is fed through a separate nip between each of the steel rolls, rolls 302 and 304, and the roll 306 having the compressible and resilient surface.

The method of the present invention may also be used to create webs of material with a virtually unlimited number of patterns of slit or particulate areas and unslit or non-particulate areas.

For example, FIG. 4 shows a web 400, such as a web of absorbent material made according to one variation of the present invention. The web of absorbent material in FIG. 4, like those appearing in a number of the figures which follow, is shown without the carrier web(s) for simplicity. The web 400 shown in FIG. 4 is provided with a zone 402 that is slit or formed into particulate material and a zone 404 which is not slit or formed into particulate material. (In the particular embodiment shown in FIG. 4, the zone 402 comprises particulate material 406 formed by slitting in two directions.) Such a web 400 can be formed by providing a pattern of teeth on the portions of the rolls that contact the zones of the web that it is desired to have slit or formed into particulate material, and omitting the pattern from the remaining portions of the rolls. In the embodiment shown in FIG. 4, the zone 402 which is slit or formed into particulate material 406 is surrounded by the zone 404 that is not slit or formed into particulate material.

FIG. 4A shows an embodiment that is the reverse of the embodiment shown in FIG. 4. In FIG. 4A, the zone 402 that is slit or formed into particulate material surrounds the portion or zone 404 of the web that is not slit or formed into particulate material. An infinite number of patterns of zones that are slit or formed into particles 406, and unslit zones are possible. FIGS. 4 and 4A show an additional advantage of the method of the present invention. With traditional compressed air particle delivery systems, it is not possible to provide a zoned particle area. The method of the present invention is advantageous in comparison to such traditional particle delivery systems in that it provides the ability to slit/particulate a web in one or more specific locations.

FIG. 5 shows a web 500, such as a web of absorbent material, made according to another variation of the present invention. The web 500 shown in FIG. 5 is provided with a plurality of bands 502 that are not slit or formed into particulate material. These bands 502 separate zones 504 that are either slit or formed into particulate material 506. Such a web 500 can be formed by providing a pattern of teeth on the portion of the rolls that contact the portion of the web that it is desired to slit or form into particulate material. The teeth are omitted from the remaining portions of the rolls. The embodiment shown in FIG. 5 provides the advantage the bands or unformed areas can be used to compartmentalize the absorbent particles 506. As shown in FIG. 5, the bands or unformed areas 502 can run in a single direction, or in more than one direction. If the bands or unformed areas 502 run in a single direction, they can be parallel to each other, or non-parallel. If the bands or unformed strips 502 run in different directions, they can be perpendicular to each other as shown in FIG. 5, or be oriented at any suitable angle with respect to each other. The bands or unformed strips 502 may be linear, curvilinear, or have some linear portions and some curvilinear portions.

In other embodiments, rather than omitting a pattern from the rolls used to slit or form the absorbent material as described for the embodiment shown in FIG. 5, a similar structure can be formed if the components of the composite web are assembled with a patterned glue area where some areas are glued and some are not. Where glue is present, the chopped absorbent foam material will be in the form of particles that are attached to the carrier web. These attached particles will form band-like structures. Where no glue is present, the chopped absorbent foam material will be in the form of "loose" particles that are contained by the band-like structures formed by the attached particles.

The method of the present invention is not limited solely to forming webs that have regions that are slit or formed into particulate material, and regions that are not slit or formed into particulate material. In other embodiments, the web can have regions with different characteristics. For instance, the entire web can be slit or formed into particulate material, but some regions may be provided with a different pattern of slitting or particulate material having different characteristics. For example, one or more regions can be provided with slits and other region(s) can be formed into particulate material. In another example, regions of the web of material can vary by the degree of engagement of the partially intermeshing teeth or the pitch of the teeth. In other cases, any two (or more) properties or characteristics provided by the method described herein could be varied over different regions of the material that will be partially or completely slit or formed into particulate material.

FIG. 5A shows an example of such a structure. FIG. 5A shows a web of absorbent material 510 that has a region along its longitudinal centerline (a "longitudinal central region") 512 that has one pattern of slits formed therein, and regions laterally outward therefrom ("longitudinal side regions") 514 and 516 that have a different pattern of slits formed therein. Such an absorbent material, which comprises part of a composite absorbent structure, could be folded into a tube-like structure similar to that shown in FIGS. 8 and 9 (described below). The folded composite absorbent structure can be inverted and attached to the body-facing side of a sanitary napkin, preferably an ultra thin sanitary napkin (which serves as a "base pad"), to form a "compound" sanitary napkin.

As shown in FIG. 5A, the longitudinal central region 512 can be provided with a plurality of transverse (or cross-machine direction) slits 518. The transverse slits 518 can be used to provide the folded tube with greater flexibility along its length than in the transverse direction. The transverse slits 518 form a plurality of transversely-oriented strips of absorbent material in the longitudinal central region 512. These strips provide the longitudinal central region 512 with the ability to preferentially wick (or transport) liquids in the transverse direction. The liquids are preferably transported to the longitudinal side regions 514 and 516 to make full use of the web of absorbent material.

The longitudinal side regions 514 and 516 are preferably provided with continuous longitudinally-oriented slits 520 to form a plurality of longitudinally-oriented strips of absorbent material. These strips provide the longitudinal side regions 514 and 516 with the ability to transport liquids in the longitudinal direction. The longitudinally-oriented slits 520 can also be used to avoid any undesirable tendencies for liquids to flow transversely out of the tube of absorbent material by establishing gaps which tend to prevent capillary transport in the transverse direction from one strip to the adjacent strip.

The absorbent material 510 shown in FIG. 5A may be formed in the following manner. A web of absorbent material 114 mm (about 4.5 inches) wide can be formed into a composite web comprising carrier web(s) as described above. A longitudinal central region that is 32 mm wide can be run through a nip between partially intermeshing rolls with teeth oriented in the transverse direction relative to the composite web. In one preferred embodiment, these teeth may have a pitch of 0.060 inches (1.5 mm) and an engagement of 0.040 inches (1 mm). The outer 41 mm on each side of the longitudinal central region 512 (which forms the longitudinal side regions 514 and 516) can be ring rolled with rolls having teeth oriented parallel to the length of the composite web. In a preferred embodiment, the teeth on these latter rolls may have a pitch of 0.060 inches (1.5 mm) and an engagement of 0.060 inches (1.5 mm).

FIG. 6 shows another example of a composite absorbent structure 600 that can be made by the method of the present invention. The composite absorbent structure 600 in FIG. 6 is shown without the carrier web(s) for simplicity. In the embodiment shown in FIG. 6, a strip of absorbent material 602 is positioned on top of a web of absorbent material 604. Placing the strip of absorbent material 602 as shown in FIG. 6 will provide a region along the longitudinal centerline of the web of absorbent material 602 that has a greater caliper than the adjacent regions 608 of the web of absorbent material. In the embodiment shown in FIG. 6, the strip of absorbent material 602 is formed into particulate absorbent material 606. The portion of the web of absorbent material lying immediately under the strip of absorbent material 602 is preferably also formed into particulate material. This will provide a double thickness of particulate of absorbent material 606 along the longitudinal centerline of the composite absorbent structure 600.

In variations of the embodiment shown in FIG. 6, the portion of the web of absorbent material 604 lying immediately under the strip of absorbent material 602 need not be formed into particulate material 606. In other variations of the embodiment shown in FIG. 6, it is also possible to form the adjacent regions 608 of the web of absorbent material 604 into particulate material 606. This will result in the entire composite absorbent structure comprising particles of absorbent material.

The embodiment shown in FIG. 6 provides a method for forming a "profiled" absorbent structure which comprises slitted or particulate material. The term "profiled", as used herein, refers to a structure having greater and lesser caliper regions. Products can easily be profiled in the longitudinal direction, the transverse direction, or any combination thereof using the method of the present invention by varying the roll patterns and absorbent material thickness.

Figure 8:
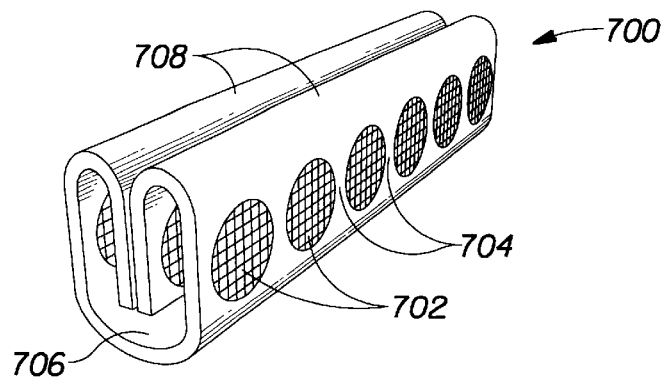
FIG. 8 shows the web of material in FIG. 7 after the same has been folded longitudinally at several places to provide a tube-like structure with spring-like structures on its sides.
Figure 9:
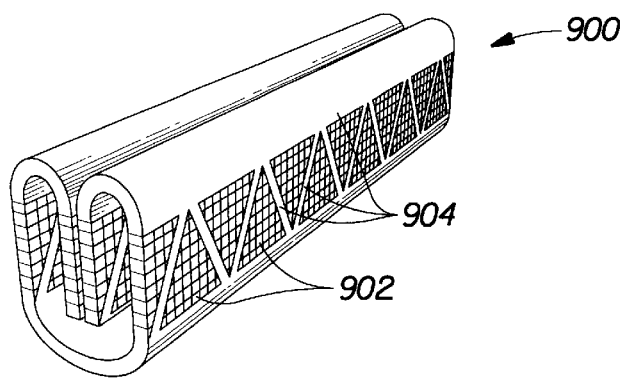
FIG. 9 shows a web of material having slit or particulate portions formed therein which has been folded similarly to the web of material shown in FIG. 8, but the slit or particulate portions are formed in a different configuration to form a truss-like structure.

FIGS. 7 to 9 show that by designing different patterns on the rolls, and optionally folding the composite web, the method of the present invention can be used to readily create structures that employ mechanical and/or civil engineering principles. Such structures include, but are not limited to lattice-like structures, wire frame mesh-like structures, trusses, I-Beam, A-Frame, or lifting springs. Such structures are useful in adding various characteristics, such as: stability, flexibility, and resiliency to the final product.

FIG. 7 shows a web of material, such as a web of absorbent material, 700 that has portions or areas 702 therein that have been slit or formed into particulate material, and portions 704 that have been left unformed. The web of material 700 is shown without the carrier web(s) for simplicity. In the embodiment shown in FIG. 7, an area 706 along the longitudinal centerline, L, of the web 700 is unformed. There are also areas 708 that lie along prospective folding lines, F, that are unformed. The web 700 is provided with a plurality of portions 702 that have been slit or formed into particulate material that are located on both sides of the longitudinal centerline, L. These portions 702 are arranged in rows on either side of the prospective folding lines, F. The areas 702 that have been slit or formed into particulate material are circular in shape. However, in other embodiments, these areas 702 can be formed in any other suitable shape.

FIG. 8 shows the web of material 700 shown in FIG. 7 after the web has been folded longitudinally in several places into a tube-like structure. The web 700 is folded along the longitudinal centerline, L, and at the folding lines, F, to form the structure shown in FIG. 8. The unformed region 706 along the longitudinal centerline adds stability to the structure. The circular portions 702 comprising particulate material along the sides of the structure provide these circular regions with increased compressibility and flexibility. The unformed regions 704 that surround the circular particulate material portions 702 provide stability to the sides of the folded structure. The particulate material will remain in place due to the presence of the carrier webs. The unformed regions 704 can act like "springs" when compressive forces are applied to the top or bottom of the folded structure. In variations of the embodiment shown in FIG. 8, the web of material may be provided with slits that run along or across the desired fold lines to provide increased flexibility for ease in folding the web and/or so that the web does not fracture where it is folded. The tube-like structure shown in FIG. 8 can be inverted and attached to the body-facing side of a sanitary napkin, preferably an ultra thin sanitary napkin (which serves as a "base pad"), to form a "compound" sanitary napkin.

FIG. 9 shows a tube-like structure formed from a web of material 900 having triangular-shaped slit or particulate portions 902 formed therein. The web of material 900 has been folded similarly to the web of material shown in FIG. 8. However, in the embodiment shown in FIG. 9, the slit or particulate portions 902 and the surrounding unformed regions 904 have different configurations to form a truss-like structure.

Figure 10:
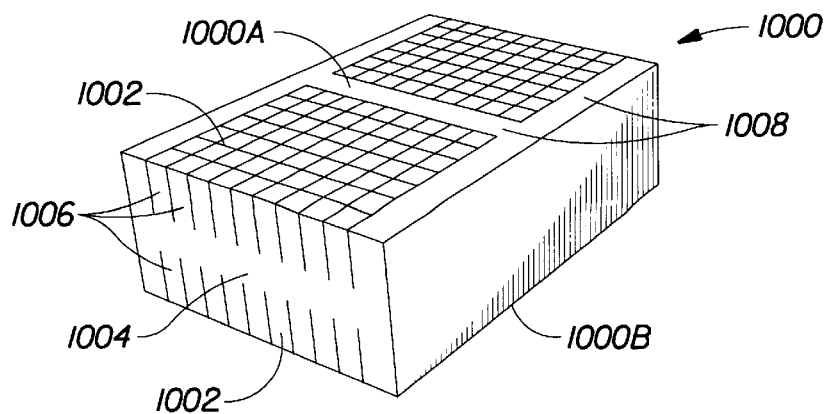
FIG. 10 shows a relatively thick piece of material that has portions of each side of its surfaces formed into slit or particulate material while the interior of the piece of material is undisturbed.

FIG. 10 shows a different type of structure comprising a web or block of material 1000 that is relatively thick. The block of material 100 shown in FIG. 10 has several surfaces. The two largest opposed surfaces are designated 1000A and 1000B. The block of material 1000 shown in FIG. 10 has portions of its thickness that extend inward from either of its surfaces 1000A and 1000B that are formed into slit or particulate material 1002 while the interior 1004 of the block 1000 is unformed. More specifically, in the embodiment shown in FIG. 10, the block 1000 is slit in two directions to form plurality of columnar elements 1006. FIG. 10 shows that the method of the present invention can be used to slit only part of the way through the thickness of a web or block of material. As shown in FIG. 10, if desired, portions 1008 on the outside and in the middle of the structure can also be left unformed to form an I-beam like structure.

An embodiment can also be created which is the opposite of that shown in FIG. 10. That is, a web or block of material can be formed that has an interior portion that is slit or formed into particulate material and an outside portion adjacent to one or more of its surfaces, that is not slit or formed into particulate material. Such a structure can be created if the outside portion(s) of the web or block of material are more resistant to fracture when the web or block is subjected to the method of the present invention. The web or block can be provided with these characteristics if, for example, the web or block comprises a foam material that is provided with a skin that is more resistant to fracture than the interior portion of the web or block of foam. Alternatively, the foam could have stratified properties (that is, it could be in the form of a stratified structure) that has an interior which is less resistant to fracture than at least one exterior portion. In any of these cases, such a structure provides the advantage that it would eliminate the need for a separate carrier web. In another variation of this alternative embodiment, the foam material having the tougher outside skin can be provided in a tube form (for example, in the form of a cylindrical tube). In such a case, the method of the present invention could be used to form a closed tube of particles or strands of material which is contained in a unitary skin.

FIG. 11 shows a web similar to that shown in FIG. 10. However, in FIG. 11, the web 1100 is thinner, and only a portion 1102 of the surface on one side of the web of material is slit. The portion 1104 that forms the other side of the web 1100 is not slit. FIG. 11A shows an example of a structure that the web of material 1100 shown in FIG. 11 can be formed into when it is bent into an arcuate configuration. As shown in FIG. 11A, when the web 1100 is bent, the slits 1106 open up between the strands of slit material 1108. The slits 1106 may provide the bent web 1100 with improved ability to acquire liquids and/or the ability to transport liquids within the channels formed by the opening of the slits 1106.

In still other embodiments, a similar structure can be formed by adhesively attaching a carrier web to only one side of an absorbent material (such as an absorbent foam material) to form a composite web. The composite web is then mechanically strained as described herein. This will slit or form the absorbent foam material into particulate material. The slit or particulate material will remain attached by the adhesive to the carrier web. The mechanical straining of the absorbent foam material will create a structure which has one side that is slit or formed into columns, and one side that is fixed to the carrier web. The side that is slit or formed into columns will tend to expand more than the side that is attached to the carrier web. This will form a structure similar to that shown in FIG. 11.

FIG. 12 shows that the method of the present invention can also be used to entangle or bond two or more layers of material. For example, in the embodiment shown, a layer of foam absorbent material 1200 is positioned between two latex bonded air-laid webs 1202 and 1204 to form a composite web 1206. In this particular embodiment, the layers of the composite web 1206 may, but need not be, bonded together. When the composite web 1206 is subjected to a mechanical straining process by impressing a patterned surface therein to compress the same, the foam 1200 will be formed into particulate material. The layers of the composite web 1206 will also be at least loosely adhered together. While not wishing to be bound to any particular theory, it is believed that the fibers of the air laid webs 1202 and 1204 will wrap around the foam particles to bind the layers together. In some cases, if the particles of foam material are subjected to liquids, they may expand and disrupt the bonds formed by the fibers wrapping around the foam particles. This may be an advantage for designs, such as those in which toilet flushablility is desired, that require a product to fall apart when totally saturated.

The compression of the composite web 1206 will result in not only at least a temporary reduction in caliper of the composite web 1206, but it may also result in an increase in the other dimensions of the composite web 1206. The composite web 1206 may, for example, comprise a foam material having an original caliper, $C_1$, of about 5 mm, which is compressed to a compressed caliper, $C_2$, of about 1 mm. After the compressive forces have been removed, the composite web 1206 may expand back to its original caliper $C_1$, or to an intermediate expanded caliper, $C_3$, between its compressed caliper and its original caliper. This Z-direction compression will also likely cause the composite web 1206 to expand in the longitudinal and transverse (X and Y) directions. Such compression may, for example, result in an increase in both length and width of the composite web of about 50%. Passing the composite web 1206 through the nip between corrugated rolls 1208 and 1210 will also deform the composite web in the Z-direction by forming corrugations into the same. This Zdirection deformation may result in an increase (e.g., of about 30%) in the overall caliper of the compressed composite web 1206 when the overall caliper is measured from the point of minimum amplitude to the point of maximum amplitude of the corrugated composite web 1206.

Figure 13:
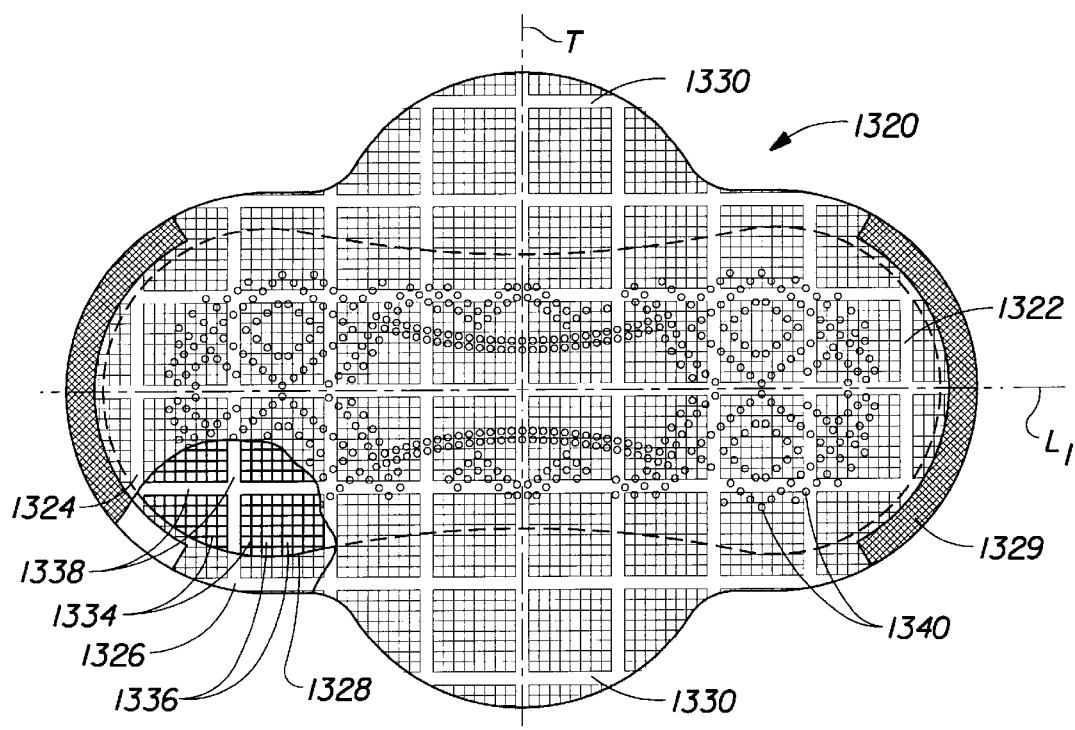
FIG. 13 shows a winged sanitary napkin that can be formed with several different features using the method of the present invention.

FIG. 13 shows an absorbent article (an extensible sanitary napkin designated 1320) in which the method of the present invention was used to simultaneously perform several different operations in the process of making the absorbent article. The sanitary napkin 1320 comprises a main body portion 1322. The main body portion 1322 comprises a liquid pervious topsheet 1324, a liquid impervious backsheet 1326 joined to the topsheet, and an absorbent core 1328 positioned between the topsheet 1324 and the backsheet 1326. These components can be joined in any suitable manner that allows the assembled sanitary napkin 1320 to be extended. The sanitary napkin 1320 may comprise a pair of end seals 1329 that are formed by fusing the topsheet and backsheet together. The sanitary napkin 1320 also has wings or flaps 1330 extending from each longitudinal side edge of the main body portion 1322 thereof.

The sanitary napkin 1320 shown in FIG. 13 has an absorbent core 1328 with regions 1334 that have been formed into particulate material 1336 by the method of the present invention. As shown in FIG. 13, the regions 1334 comprising the particulate material are separated by unformed bands 1338 that are oriented in both the longitudinal direction and the transverse direction. In addition, the method of the present invention was preferably also used to form strainable network regions into the topsheet 1324 and the backsheet 1326. The term "strainable network region" is described in greater detail in U.S. Pat. No. 5,518,801 entitled Web Materials Exhibiting Elastic-Like Behavior, which issued to Chappell, et al. on May 21, 1996. The formation of the strainable network regions into the topsheet 1324 and backsheet 1326 provides these components of the sanitary napkin with extensibility. The unformed bands of the strainable network in the topsheet 1324 and backsheet 1326 provide these extensible components with elastic-like properties. The formation of the absorbent core 1328 into particulate material places the absorbent core 1328 into a form that will not interfere with the extensibility of the topsheet 1324 and backsheet 1326.

The topsheet 1324 and backsheet 1326 can be provided with extensibility in one direction, in more than one direction, or in all directions in the X-Y plane, depending on the pattern of the strainable network formed therein. In the embodiment shown in FIG. 13, the sanitary napkin 1320 is extensible in both the longitudinal and transverse directions. The sanitary napkin 1320 shown in FIG. 13 is preferably extensible in the amounts specified in the disclosure of U.S. Pat. No. 5,611,790 entitled "Stretchable Absorbent Articles", which issued to Osborn, et al. on Mar. 18, 1997.

FIG. 13 shows that the method of the present invention can also be used to provide the wings or flaps 1330 with extensibility. The wings 1330 can be provided with extensibility in any of the directions specified above for the topsheet and backsheet. It is also possible to provide the wings 1330 with extensibility in a direction or amount that differs from that of the topsheet and backsheet by passing the sanitary napkin 1320 through an apparatus that has a different pattern on the portion of the patterned surface that contacts the wings 1330 from the portion of the apparatus that contacts the main body portion of the absorbent article. The portions of the rolls that will be used to provide the wings with extensibility, if mating rolls are used, may also be positioned closer together, or engage to a greater extent, if the wings 1330 do not have as many layers as the main body portion 1322 does.

The method of the present invention can also be used to emboss and/or bond the components of the sanitary napkin together. FIG. 13 shows that the body-facing surface of the sanitary napkin 1320 may be provided with a plurality of embossments in the form of fusion bonds 1340. The fusion bonds 1340 can be formed by providing a plurality of bonding elements on the patterned surface of the apparatus used to form the absorbent core 1328 into particulate material. The bonding elements may optionally be heated if desired. Typically, in order to bond the components together, at least those components that are bonded together will preferably comprise at least some thermoplastic material. In other embodiments, it may be desirable for the patterned surface to be provided with elements that merely emboss the body-facing surface of the sanitary napkin, and do not form fusion bonds between the components thereof.

The method of the present invention can, thus, be used to form the absorbent core 1328 into particulate material, provide the topsheet 1324 and backsheet 1326 with extensibility, provide the wings or flaps 1330 with extensibility, to emboss and/or bond the components together, and seal the ends of the sanitary napkin 1320. This can all be accomplished in a single pass through an apparatus similar to that shown in FIG. 3.

The method of the present invention is, thus, capable of making extensible structures which previously could only be made with great difficulty. This is due to the fact that the method is able to slit, chop, or otherwise break the integrity of the absorbent material. Previously, it was difficult to impart sufficient extensibility to absorbent materials by forming a strainable network into the same. Slitting, chopping, or breaking the absorbent material provides an absorbent article with absorbent material that does not significantly interfere with the desired extensibility properties imparted to the topsheet and backsheet when a strainable network is formed into the topsheet and backsheet.

Figure 14:
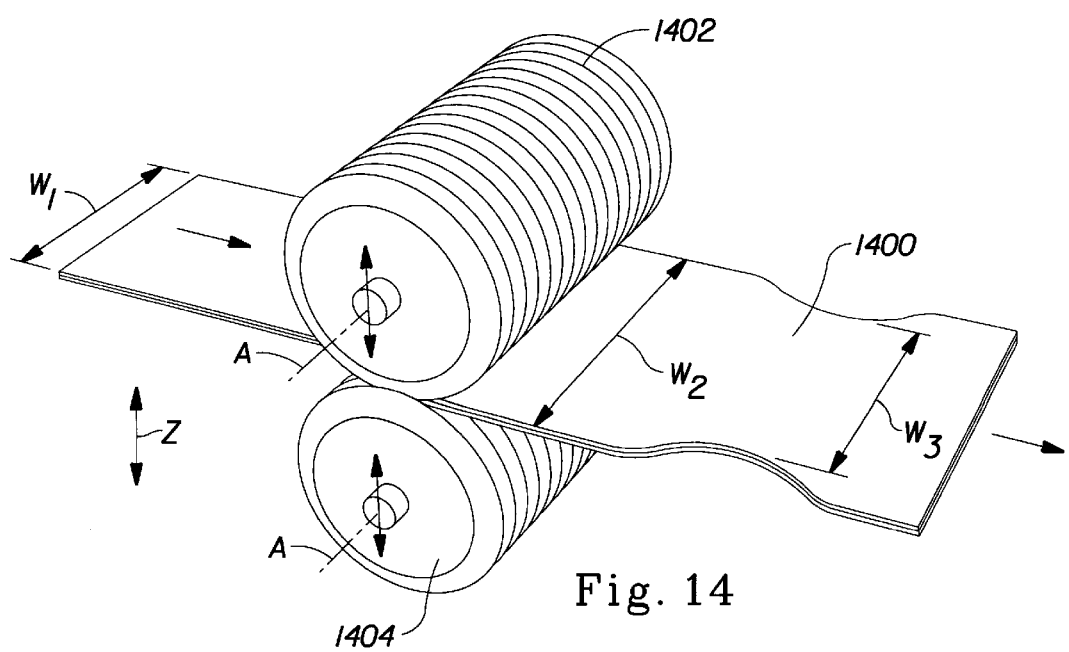
FIG. 14 is a simplified perspective view showing an alternative embodiment in which the method of the present is used to make an hourglass-shaped web of slitted absorbent material for use in diapers.

FIG. 14 shows an alternative embodiment of the method of the present invention which is used to make an hourglass-shaped web of slitted or particulate absorbent material 1400.

FIG. 14 shows an apparatus suitable for slitting an absorbent material. The apparatus comprises a pair of meshing rolls 1402 and 1404. Any suitable pattern can be provided on the surfaces of the rolls. The rolls 1402 and 1404 shown in FIG. 14 are preferably similar to those shown in FIGS. 1 and 3, only without the channels 46 in the bottom roll. It has been found that if the distance between the rolls is increased or decreased, this will in addition to slitting or chopping the absorbent material, also vary the overall width of the slit or chopped web of material 1400. It has been found that when the rolls are moved closer together in the Z-direction, this will increase the percentage of engagement of the teeth on the rolls, and create a wider web of slit or particulate material. Thus, for example, if the initial width $W_1$ of the web of absorbent material is 75 mm, it has been found to be possible to increase the width of such a web to widths as great as 125 mm. If the opposite is done (that is, the rolls are moved further apart, the web of slit or particulate material will be narrower in width.

In the embodiment of the method shown in FIG. 14, this concept has been taken a step further. The distance between the pair of rolls shown in FIG. 14 is cyclically increased and decreased. The cyclical increase and decreasing of the space between the rolls can be accomplished in several ways. These include, but are not limited to utilizing a cam arrangement, a solenoid, or by profiling the rolls. This forms the web of absorbent material into a web of slitted or particulate material that is provided in a plurality of hourglass shaped portions that may be cut into individual absorbent cores. The shaped absorbent core can be used in a wide variety of types of absorbent articles.

Figure 15:
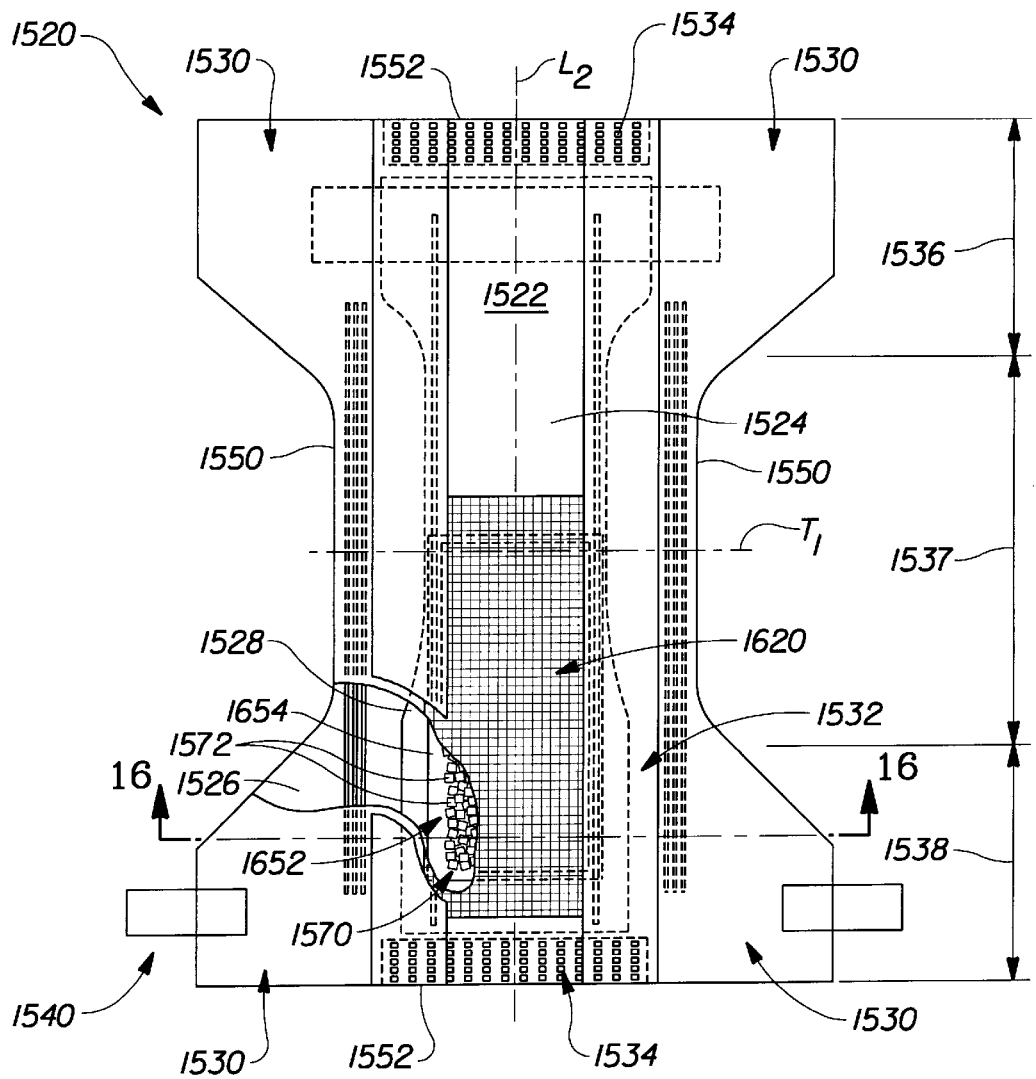
FIG. 15 is a partially fragmented top plan view of a diaper having an hourglass shaped absorbent core that comprises particulate absorbent material.

FIG. 15 shows such an hourglass absorbent core in place in a diaper 1520. As shown in FIG. 15, the diaper 1520 preferably comprises a liquid pervious topsheet 1524; a liquid impervious backsheet 1526; an absorbent core 1528, which is preferably positioned between at least a portion of the topsheet 1524 and the backsheet 1526; side panels 1530; elasticized leg cuffs 1532; an elastic waist feature 1534; and a fastening system generally designated 1540. The diaper 1520 shown in FIG. 15 has a first waist region 1536, a second waist region 1538 opposed to the first waist region 1536 and a crotch region 1537 located between the first waist region and the second waist region. The periphery of the diaper 1520 is defined by the outer edges of the diaper 1520 in which the longitudinal edges 1550 run generally parallel to the longitudinal centerline $L_2$ of the diaper 1520 and the end edges 1552 run between the longitudinal edges 1550 generally parallel to the transverse centerline $T_1$ of the diaper 1520.

Figure 16:
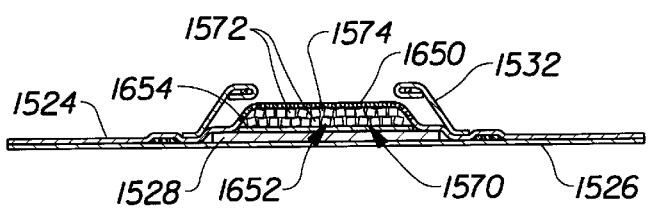
FIG. 16 is a cross-sectional view of the diaper shown in FIG. 15 taken along line 16—16 of FIG. 15.
Figure 16A:
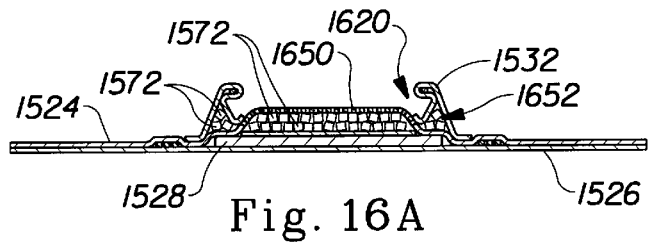
FIG. 16A is a cross-sectional view of an alternative embodiment of the diaper shown in FIGS. 15 and 16.

The diaper 1520 shown in FIG. 15 preferably comprises a waste management element 1620 that is capable of accepting, storing and/or immobilizing viscous fluid bodily waste, such as runny feces. The waste management element 1620, and the components thereof, can be located anywhere in the diaper, including the crotch region or either waist region, or it may be operatively associated with or included in any structure or element such as the core 1528, or as shown in FIG. 16A, a leg cuff, or some other element.

The waste management element 1620 preferably comprises an acceptance element 1650 for accepting bodily exudates, particularly viscous fluid bodily waste. Suitable materials and structures for use as the acceptance element 1650 may include apertured nonwoven webs, apertured films, apertured formed films, scrims, woven webs, scrim, netting, macroporous thin foams, and the like. The waste management element 1620 preferably also comprises a storage element 1652 that is capable of storing viscous bodily waste accepted by the acceptance element 1650. The embodiment of the storage element 1652 shown in FIGS. 15, 16, and 16A comprises a macro-particulate structure 1570 comprising a multiplicity of discrete particles 1572 arranged in an orderly array.

The expression "orderly array", as used herein, includes distributions of particles that are at least roughly aligned with their sides oriented in the same general direction. The particles may also be at least roughly arranged in rows and/or layers.

The macro-particulate structure 1570 may include any number of particles 1572. Further, the particles 1572 may be unjoined and free to move within the structure 1570 or may be joined to each other by any known means. Alternatively, the structure 1570 may include an external support, such as a meltblown hot-melt glue, a web, a netting, a scrim, a thread or other adhesive or nonadhesive entangling supports. Any of the particles 1572 may also be joined with any other portion of the diaper structure, such as the topsheet or the core. The particles 1572 may also be constrained in patterned, three-dimensional regions such as pleats, "pillows", and pockets.

The individual particles 1572 may be made from any material suitable for use in absorbent articles. The materials used in the particles 1572 may be absorbent, nonabsorbent, microporous, macroporous, resilient, nonresilient, etc. or may have any other desirable characteristic. Examples of macroporous absorbent materials suitable for use in the particles 1572 include highloft nonwovens, open cell foams, bundles of fibers, sponges and the like. Other absorbent materials include cellulosic batts, capillary channel fibers, osmotic storage materials such as super absorbent polymers, etc. Nonabsorbent particles 1572 may comprise plastic, metal, ceramic, glass, closed cell foams, column packing materials, synthetic fibers, gels, encapsulated gas, liquids and the like. Further, any or all of the particles 1572 may include odor absorbents, lotions, skin care formulations, antimicrobials, pH buffers, enzyme inhibitors, and the like.

The macro-particulate structure 1570 preferably includes a continuous interstitial void space 1574 that is defined by the space between the particles 1572. By varying the size and/or shape of the particles 1572, the interstitial void space 1574 can be controlled. The particles may be of any known shape, including spheres, oblate spheroids, rectangular and polygonal solids, and the like. Suitable particle shapes and corresponding void fractions are described in Perry's Chemical Engineering Handbook, $6^{th}$ ed., McGraw-Hill, 1984, at p. 18–20. The diaper shown in FIGS. 15 and 16A and B is described in greater detail in U.S. patent application Ser. No. 08/970,508 entitled "Diaper With Improved Feces Management Properties", filed in the name of Roe, et al. on Nov. 11, 1997.

The topsheet 1524 and/or the backsheet 1526 of the diaper 1520, or any portion thereof, may be elastically extensible in one or more directions. In one embodiment, the topsheet 1524 and/or the backsheet 1526 may comprise a structural elastic-like film ("SELF") web to provide an extensible diaper. A structural elastic-like film web is an extensible material that exhibits an elastic-like behavior in the direction of elongation without the use of added elastic materials. The SELF web includes a strainable network having at least two contiguous, distinct, and dissimilar regions. Preferably, one of the regions is configured so that it will exhibit resistive forces in response to an applied axial elongation in a direction parallel to the predetermined axis before a substantial portion of the other region develops significant resistive forces to the applied elongation. At least one of the regions has a surface-pathlength which is greater than that of the other region as measured substantially parallel to the predetermined axis while the material is in an untensioned condition. The region exhibiting the longer surface-pathlength includes one or more deformations which extend beyond the plane of the other region.

The SELF web exhibits at least two significantly different stages of controlled resistive force to elongation along at least one predetermined axis when subjected to an applied elongation in a direction parallel to the predetermined axis. The SELF web exhibits first resistive forces to the applied elongation until the elongation of the web is sufficient to cause a substantial portion of the region having the longer surface-pathlength to enter the plane of applied elongation, whereupon the SELF web exhibits second resistive forces to further elongation. The total resistive forces to elongation are higher than the first resistive forces to elongation provided by the first region. SELF webs suitable for use on the diaper 1520 shown in FIG. 15 are more completely described in U.S. Pat. No. 5,518,801 entitled Web Materials Exhibiting Elastic-Like Behavior, which issued to Chappell, et al. On May 21, 1996, which is incorporated herein by reference. In alternate embodiments, the topsheet and/or the backsheet 1526 may comprise elastomeric nonwovens, films, foams, strands, or combinations of these or other suitable materials with nonwovens or synthetic films.

Alternative types of elastically extensible absorbent structures suitable for use in a diaper (or other type of absorbent article) can also be created using the method of the present invention. One preferred alternative structure is formed by including an elastically extensible material in the composite web prior to subjecting the composite web to a force when carrying out the method of the present invention. The elastically extensible material can comprise any suitable elastically extensible material. The elastically extensible material can be liquid pervious, or if it will be located on a garment-facing side of the absorbent material, liquid impervious. Suitable elastically extensible materials include any of those elastically extensible materials specified as being suitable for use as a carrier web. An elastically extensible material can be selected that is extensible in one direction, or more than one direction. The elastically extensible material may, but need not be as wide and/or as long as the other components of the composite web.

Such an elastically extensible material can be positioned between the first carrier material 20 and the destructible absorbent material 22. Alternatively, the elastically extensible material can be positioned between the second carrier material 24 and the absorbent material. In other variations of this embodiment, the elastically extensible material can be positioned between both carrier materials 20 and 24 and the absorbent material 22. In still other versions of such an alternative embodiment, one or more of the carrier webs can comprise the elastically extensible material.

In one particularly preferred embodiment of such an elastically extensible structure, the composite absorbent structure looks similar to the composite web shown in FIG. 3, only it comprises a five layer structure. The five layer composite absorbent structure comprises from top to bottom: a topsheet material, a layer of elastic polyurethane foam, a layer of absorbent foam material described in the Absorbent Foam Material patents, another layer of elastic polyurethane foam, and a backsheet material. The composite absorbent structure is then subjected to the method of the present invention. The method of the present invention can be used to either slit or form the layer of absorbent foam material into particulate material. This will form an elastically extensible composite absorbent structure in which the absorbent foam material is either slit into a plurality of strips, or formed into particulate material. The other layers of the composite absorbent structure (including the elastic polyurethane foam layers) will typically only be corrugated by this process. However, embodiments in which one or more of these layers is also at least partially slit are not precluded.

The elastically extensible absorbent structure formed in this manner can have numerous uses. The elastically extensible absorbent structure can serve as a stand-alone absorbent article, or it can comprise a portion or feature of an absorbent article. For example, the elastically extensible structure can comprise a portion which forms (all or a portion of) an elastic waist feature for a diaper and a portion which forms (all or a portion of) an absorbent core for a diaper. The portion of the elastically extensible structure that forms the elastic waist feature may, but need not, comprise an absorbent foam material. The method of the present invention can, thus, be used to form a bendable, flexible, stretchable, and if desired, absorbent, elastic waist feature that is highly comfortable and conformable to the wearer's body. The portion of the elastically extensible absorbent structure that forms all or part of the absorbent core of the diaper in addition to absorbency, will have similar properties.

Figure 17:
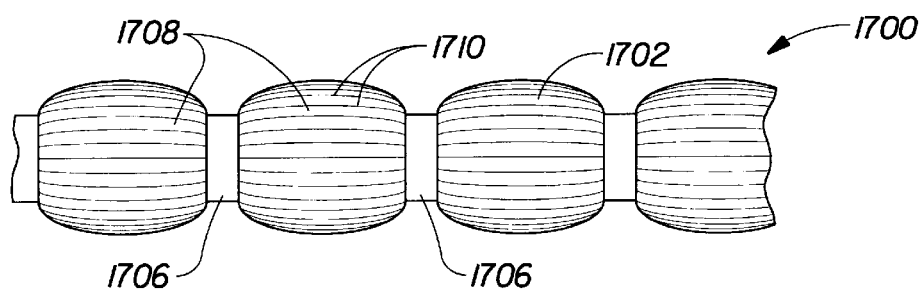
FIG. 17 is a side view of a segmented structure that is formed from an expandable material which is surrounded by a wrapping material, which was made using the method of the present invention.

FIG. 17 shows another example of a structure 1700 that can be formed by the method of the present invention. The structure shown in FIG. 17 comprises an outer carrier web or wrapping 1702 (such as one of the carrier webs described above). The wrapping 1702 is wrapped around a compressible and resilient material (such as one of the foam absorbent materials described above). The outer wrapping 1702 has a strainable network formed therein. The strainable network comprises a plurality of substantially planar unformed first regions 1706, and a plurality of second regions 1708 formed into raised rib-like elements 1710. In the embodiment shown in FIG. 17, the unformed regions 1706 are in the form of bands that intermittently encircle the formed regions 1708. The embodiment shown in FIG. 17 is preferably made by forming a laminate of the outer wrapping 1702 and the compressible and resilient material. The strainable network region is preferably then formed in the laminate of the outer wrapping 1702 and the compressible and resilient material. The outer wrapping 1702 is then wrapped around the compressible and resilient material quickly enough so that the wrapping occurs before the compressible and resilient material begins to expand.

As shown in FIG. 17, when the compressible and resilient material expands, it expands more into the areas where the second regions 1708 of the strainable network region are formed (due to the greater extensibility of these regions of the wrapping 1702). The expansion causes these regions to bulge further outward than the unformed regions 1706. This provides a segmented structure. The segmented structure shown in FIG. 17 is advantageous for use in absorbent articles or as an absorbent article (such as an absorbent interlabial device) in which it is desirable to provide an absorbent article with areas having greater flexibility (the smaller diameter unformed regions 1706) than other regions. Such a segmented structure may provide improved conformity with the shape of the wearer's body when worn.

Figure 18:
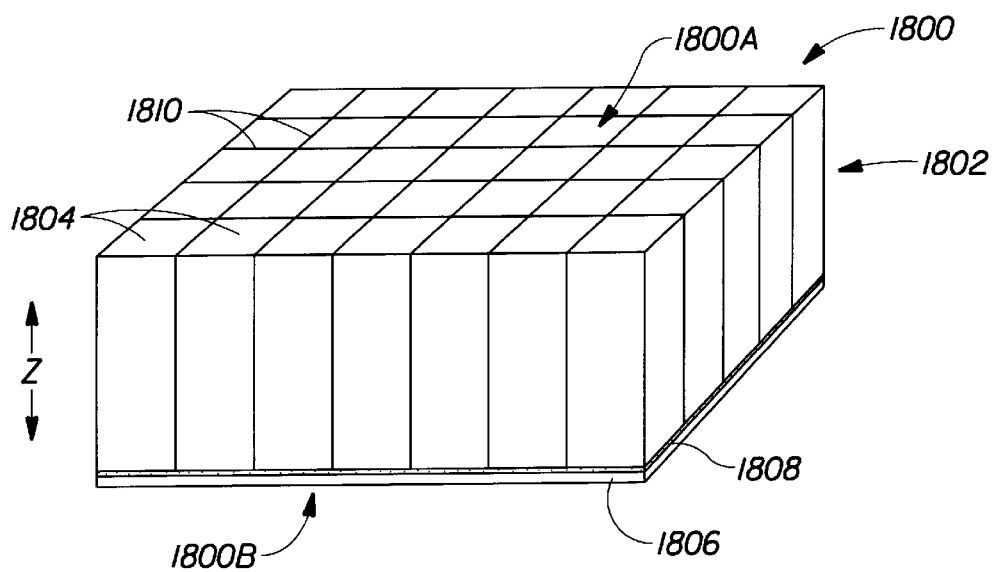
FIG. 18 is a simplified perspective view of a portion of a structure in which a plurality of columns of material extend from a backing, which was made using the method of the present invention.

FIG. 18 shows another type of structure or absorbent article 1800 that the method of the present invention can be used to form. The absorbent article, or portion of an absorbent article 1800 shown in FIG. 18 comprises a composite structure such as a web or block of material 1802 that is formed into a plurality of upright columns 1804. The columns 1804 can have any suitable dimensions be very narrow if desired. The columns 1804 may comprise absorbent foam material. The columns 1804 may be attached to a carrier web 1806 of the type described herein. The absorbent article shown in FIG. 18 provides a structure in which the orientation of the structural components making up the structure is primarily oriented perpendicular to the plane of the absorbent article (that is, in the Z-direction).

The absorbent structure 1800 shown in FIG. 18 is distinguishable from conventional fibrous webs in which the structural elements comprising the fibrous webs (the individual fibers) are typically stacked on top of one another (or oriented in the X-Y plane). The absorbent structure shown in FIG. 18 provides the absorbent article with increased surface area for the absorption of discharged bodily liquids and natural void spaces 1810 between the columns 1804 that can serve to acquire gushes of such fluids and/or take in solid matter such as that in bowel movements or cellular debris contained in menstrual fluid. If desired, the columns of absorbent material can be placed directly against the wearer's body to serve as a "topsheet" for the absorbent article.

To make the absorbent structure shown in FIG. 18, a composite web can be formed of a web or block of absorbent material which is adhesively attached (to the extent possible) to a carrier web by adhesive 1808. The composite web thus formed is subjected to a force by impressing a patterned surface therein. The surface of the composite web adjacent to the exposed surface of the absorbent material can either be temporarily or permanently covered with a web for ease in removing the composite web from the patterned surface. If a web is used to temporarily cover the surface of the absorbent material, it can be removed after the composite web is removed from the patterned surface. The adhesively attached carrier web 1806 may be liquid impervious and, thus, may serve as a liquid impervious backsheet. The absorbent structure shown in FIG. 18 is advantageous in that it provides a body-facing surface that is highly conformable to the adjacent portions wearer's body.

Figure 19:
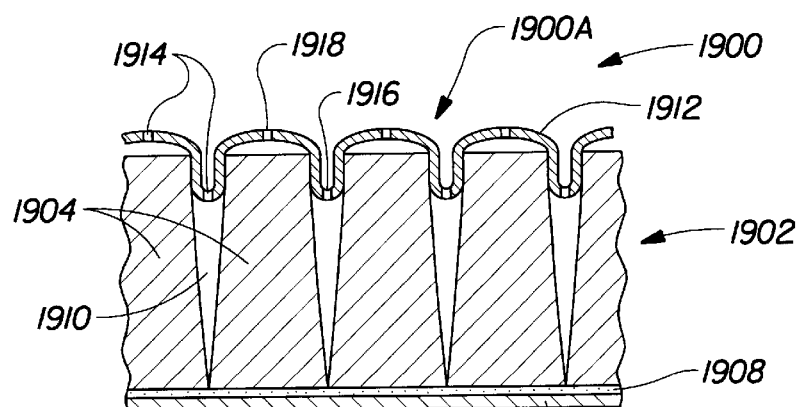
FIG. 19 is a schematic side view of a portion of a variation of the structure shown in FIG. 18, in which a cover, such as a topsheet, is draped over the columnar elements thereof.

FIG. 19 shows another example of a structure 1900 that can be formed by the method of the present invention. The structure 1900 shown in FIG. 19 is similar to that shown in FIG. 18. The structure 1900 shown in FIG. 19 has a body-facing surface 1900A and a back surface 1900B. The structure also comprises a web or block of material 1902 that is formed into columns 1904, which is joined to a carrier web 1906 by an adhesive 1908. The columns 1904 also have void spaces 1910 therebetween. However, in FIG. 19, a liquid pervious carrier web 1912 is placed on the top of the absorbent foam material 1902. As shown in FIG. 19, the mechanical straining can force or tuck portions of the liquid pervious carrier web 1912 between the columns 1904. The liquid pervious carrier web 1912 can, as shown in FIG. 19, be tucked partially downward toward the carrier web 1906 that serves as a backing. In other embodiments, the liquid pervious carrier web 1912 can be tucked all the way down to the backing 1906 (and if desired, joined thereto).

The portions of the liquid pervious carrier web 1912 that are tucked between the columns 1904 can be provided with apertures, generally designated 1914, as can the portions of the liquid pervious carrier web 1912 that overlie the tops of the columns 1904. These apertures 1914 can be of any suitable shape and size. The apertures 1914 can be circular, slits, etc. The apertures 1914 can all be the same size. Alternatively, different size apertures may be used. For example, the portions of the liquid pervious carrier web 1912 that are tucked between the columns 1904 can be provided with larger apertures (or macro apertures) 1916, while the portions of the liquid pervious carrier web 1912 that overlie the tops of the columns can be provided with smaller apertures (or micro apertures) 1918. In the embodiment shown in FIG. 19, however, the apertures 1916 and 1918 in these different locations are of the same size.

Figure 20:
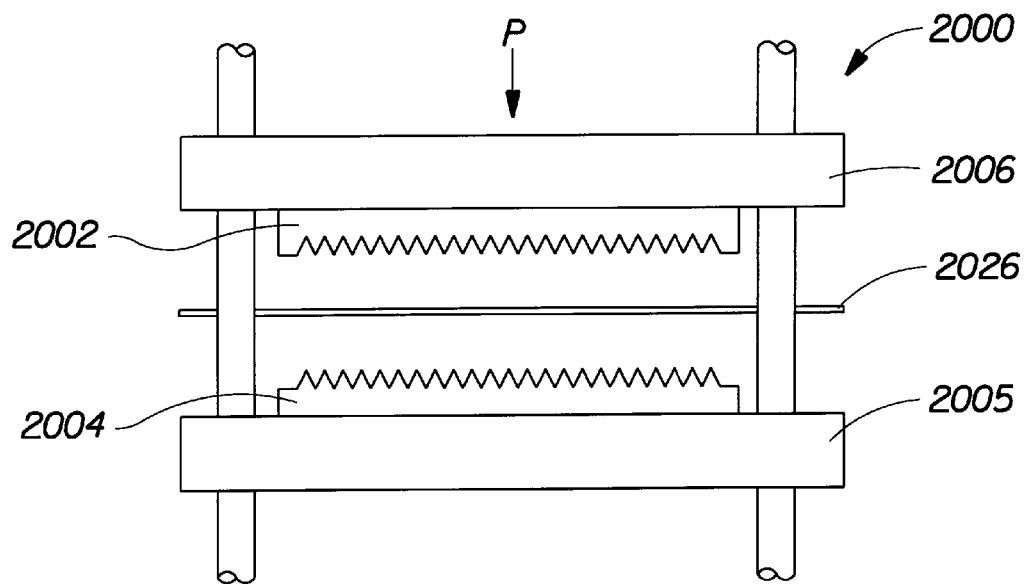
FIG. 20 is a schematic side view of a portion of another apparatus that can be used to carry out the method of the present invention, which apparatus comprises a pair of mating plates, each of which has a surface with a plurality of teeth thereon.

FIG. 20 shows an alternative embodiment of the method of the present invention in which an embossing process is used. In the embodiment shown in FIG. 20, the composite web 2026 is placed in an apparatus 2000, and subjected to pressure. The apparatus comprises a pair of plates 2002 and 2004 that are attached to movable platens 2006 and 2005, respectively. Each of the plates has a pattern of teeth on its surface. The embossing process shown in FIG. 20 provides a greater degree of flexibility in that it may be more easily capable of forming more complicated patterns, such as slits in the form of diagonal lines, into the absorbent material, which are difficult to form using rolls having intermeshing teeth.

Figure 21:
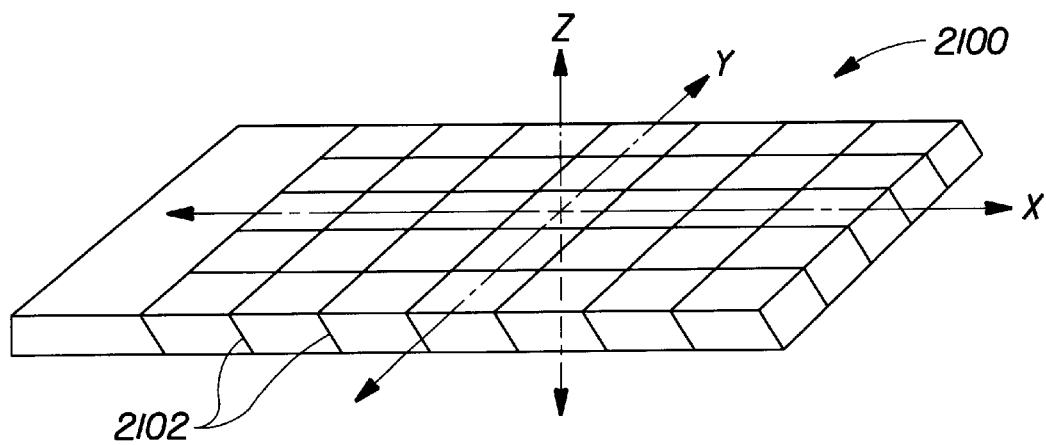
FIG. 21 is a perspective view of a layer of absorbent material which has a portion that is provided with a plurality of slits therein that are oriented at an angle to the plane of the material.

FIG. 21 shows that in other embodiments of the method of the present invention, it is possible to form slits 2102 in the absorbent material 2100 that are oriented at an angle to the plane of the absorbent material (the X-Y plane in FIG. 21). A portion of the absorbent material 2100, at the left side of the same is left unslit for comparison. The use of plates, rather than rolls, also provides the ability to more easily form such structures.

Figure 22:
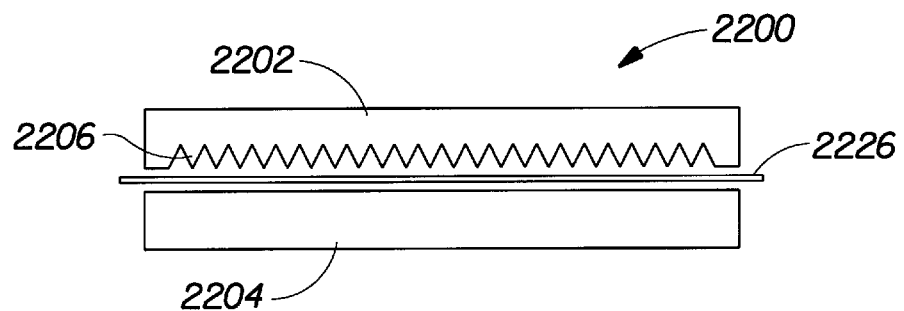
FIG. 22 is a schematic side view of a portion of another apparatus that can be used to carry out the method of the present invention which comprises a plate which has a pattern on its surface, and an opposing flat plate.

FIG. 22 shows another alternative embodiment of the method of the present invention in which an embossing process is used. In the embodiment shown in FIG. 22, the composite web 2226 is placed in an apparatus, and subjected to pressure. The apparatus 2200 also comprises a pair of plates, 2202 and 2204. However, only one of the plates, upper plate 2202, has a pattern of teeth 2206 on its surface. The other plate, flat plate 2204, does not. The flat plate 2204 can have a rigid surface, or a deformable surface.

Figure 23:
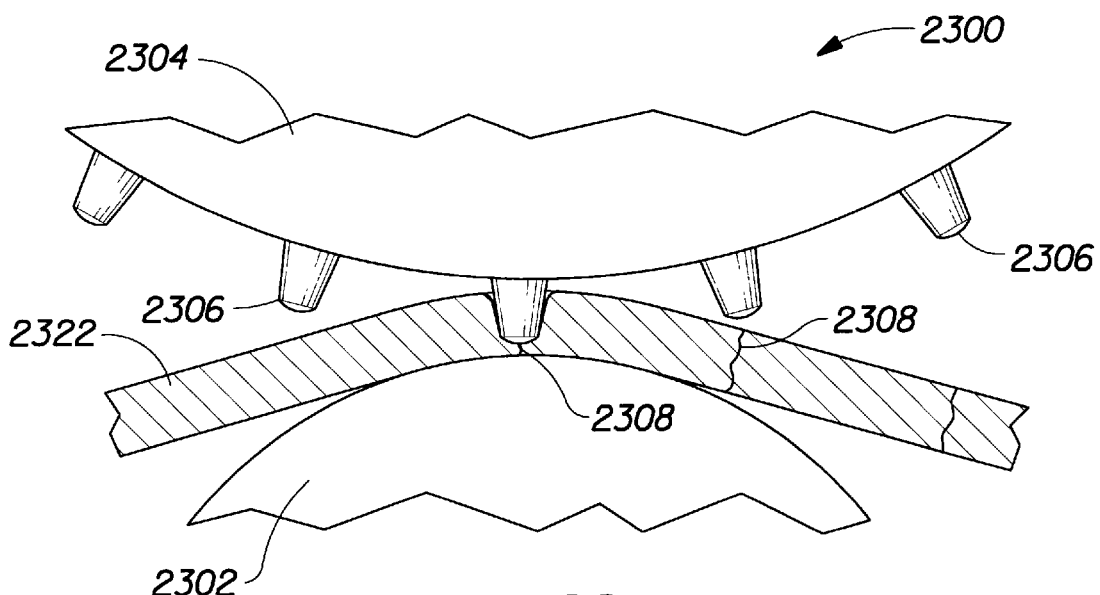
FIG. 23 is a side view of a portion of another apparatus that can be used to carry out the method of the present invention which comprises a patterned roll and an anvil roll, which may be similar to an apparatus used to spot bond nonwoven materials.

FIG. 23 shows another alternative embodiment of the method of the present invention. In the embodiment shown in FIG. 23, the apparatus 2300 comprises an anvil roll 2302 and a patterned roll 2304 that has a plurality of elements 2306 which have a small surface or "land" area. This apparatus 2300 could be similar to an apparatus used to spot bond nonwoven materials. The embodiment in FIG. 23 shows the absorbent material 2322 without the carrier web (s) for simplicity of illustration. This embodiment shows that the compression of the absorbent materials 2322 in very small areas may not result in any noticeable amount of absorbent material being removed from the area where localized pressure is exerted on the material. Instead, the localized pressure causes fractures 2308 to develop in the absorbent material 2322 that emanate from the points where localized pressure has been applied. The fractures 2308 may or may not be visible. The fractures 2308 also may not extend completely through the absorbent material 2322. If the absorbent material 2322 is stretched after it is passed through the apparatus 2300 shown in FIG. 23, the fractures 2308 may expand and propagate so that they are visible.

In other embodiments, particularly where the absorbent material is slit with a plurality of intermittent slits, the absorbent material can be stretched simultaneously with the slitting, or thereafter. This will create openings in the absorbent material.

Certain slitting patterns combined with stretching to widen the slits can form the slit absorbent material into a structure that resembles an "expanded metal" structure with diamond-shaped openings. The openings can then, if desired, be filled with particles of absorbent material.

In still other embodiments, the materials used herein, or the method of the present invention can be altered so that a wider variety of materials will be suitable for use in this method. For example, the materials that are described herein as being suitable for being broken, slit, or formed into particulate material, are generally those that are capable of being fractured in these manners in their natural state, at room temperature. In other embodiments, materials that have a higher breaking point (or are less brittle) than those described herein could be altered so that they can be fractured. For instance, polymeric materials that have these characteristics could be treated with a solvent to selectively strip out components of the polymer to make the polymeric material more brittle at room temperature. Alternatively, or additionally, the material that is to be fractured can be irradiated (e.g., treated with UV light) to make it more brittle. Alternatively, or additionally, the material that is to be fractured could be chilled to a temperature that is below room temperature to make it more susceptible to fracturing. These treated materials can then be combined one or more carrier webs to form the composite web that is processed according to the present invention. In still other variations of such an embodiment, the material that is to be fractured can be the same type of material as that used for the carrier web(s), only the piece or web of material that will be fractured can be treated in one of these manners before it is combined into a composite web. In still other embodiments, the carrier material could be treated to increase its breaking point.

In still other embodiments, the variations of the method described herein can be combined to create additional embodiments. The structures described herein can also be combined in any suitable manner to create additional structures. In addition, although the method of the present invention is directed primarily to slitting or forming absorbent material into particulate material, it is also possible to use the method of the present invention to slit or form non-absorbent material into particulate material.

The disclosures of all patents, patent applications (and any patents which issue thereon, as well as any corresponding published foreign patent applications), and publications mentioned throughout this description are hereby incorporated by reference herein. It is expressly not admitted, however, that any of the documents incorporated by reference herein teach or disclose the present invention.

While particular embodiments of the present invention have been illustrated and described, it would be obvious to those skilled in the art that the various other changes and modifications can be made without departing from the spirit and scope of the invention.

What is claimed is:

1. A method of fracturing an absorbent material in situ on another material in a process of making an absorbent element for an absorbent article, said method comprising the steps of:
   (a) providing a carrier material in the form of a web having a first breaking point;
   (b) providing a second material on said carrier material and joinings said material to form a composite structure having two surfaces, said second material having a second breaking point that is lower than the breaking point of said carrier material, said second material comprising an absorbent material;
   (c) providing an apparatus for applying a force to said composite structure; and
   (d) applying a localized force to at least a portion of at least one of the surfaces of said composite structure using said apparatus, said force being greater than the second breaking point, but less than said first breaking point so that the absorbent material fractures in at least one place without breaking the carrier material.

2. The method of claim 1 wherein said absorbent material at least partially breaks in said at least one place and separates adjacent a break in said absorbent material.

3. The method of claim 1 wherein said force applied to said composite structure in step (d) has a tensile force component.

4. The method of claim 1 wherein said force applied to said composite structure in step (d) has a compressive force component.

5. The method of claim 1 wherein said force applied to said composite structure in step (d) is a combination of a compressive force and a tensile force.

6. The method of claim 1 wherein said apparatus comprises a pair of rolls having partially intermeshing teeth thereon, and said rolls define a nip therebetween.

7. The method of claim 1 wherein said absorbent material in said composite structure is provided with a plurality of slits therein and said carrier material is not slit.

8. A method of fracturing an absorbent material in situ on a carrier material in a process of making an absorbent element for an absorbent article, said method comprising the steps of:
   (a) providing a carrier material in the form of a web;
   (b) providing an absorbent material on said carrier material to form a composite structure having two surfaces, wherein the carrier is adjacent to said absorbent material and the absorbent material has been treated to reduce its breaking point, said absorbent material having been treated to reduce its breaking point to one that is lower than the breaking point of said carrier material,
   (c) providing an apparatus for applying a force to said composite structure; and
   (d) applying a localized force to at least a portion of at least one of the surfaces of said composite structure using said apparatus, said force being greater than the second breaking point of the absorbent material, but less than said first breaking point of the carrier material so that the absorbent material fractures in at least one place without breaking the carrier material.

9. A method of slitting a web of material in situ on another web of material in a process of making at least a portion of an absorbent article, said method comprising the steps of:
   (a) providing a carrier material in the form of a web having a first yield to break point under tensile forces;
   (b) providing an absorbent second material on said carrier web and joining said material to form a composite structure, said absorbent second material having a second yield to break point under tensile forces that is lower than the yield to break point of said carrier material;
   (c) providing an apparatus for mechanically straining said composite structure, said apparatus having at least one patterned surface thereon; and
   (d) subjecting said composite structure to a mechanical straining process using said apparatus by impressing the at least one patterned surface thereon with a force that is greater than the second yield to break point, but less than said first yield to break point so that the second material is at least partially slit without slitting the carrier material.

10. The method of claim 9 wherein said carrier material comprises a nonwoven material.

11. The method of claim 9 wherein said carrier material comprises an apertured film.

12. The method of claim 9 wherein said apparatus comprises a pair of rolls having partially intermeshing teeth thereon.

13. A method of making a self-contained web of particulate material, said method comprising the steps of:
   (a) providing a carrier web in the form of a web having a first yield to break point under tensile forces;
   (b) providing a second web of material for forming into particulate material on said carrier web and joining said material to form a composite web, said second web of material having a second yield to break point under tensile forces that is lower than the yield to break point of said carrier web;
   (c) providing an apparatus for mechanically straining said composite web, said apparatus having at least one patterned surface thereon; and
   (d) subjecting said composite web to a mechanical straining process using said apparatus by impressing the at least one patterned surface thereon so that the second web of material is at least partially formed into particulate material without forming the carrier web into particulate material.

14. The method of claim 13 wherein said second web of material comprises an absorbent material.

15. A method of making a self-contained web of particulate material, said method comprising the steps of:
   (a) providing a carrier web in the form of a web having a first yield to break point under tensile forces;
   (b) providing a second web of material for forming into particulate material on said carrier web to form a composite web, said second web of material comprising an absorbent foam material having a second yield to break point under tensile forces that is lower than the yield to break point of said carrier web;
   (c) providing an apparatus for mechanically straining said composite web, said apparatus having at least one patterned surface thereon; and
   (d) subjecting said composite web to a mechanical straining process using said apparatus by impressing the at least one patterned surface thereon so that the second web of material is at least partially formed into particulate material without forming the carrier web into particulate material.

16. The method of claim 13 wherein said carrier web comprises a nonwoven material.

17. The method of claim 13 wherein said carrier web comprises an apertured film.

18. A method of making a self-contained web of particulate material, said method comprising, the steps of:
(a) providing a carrier web in the form of a web having a first yield to break point under tensile forces;
(b) providing a second web of material for forming into particulate material on said carrier web to form a composite web wherein said carrier web and said second web are joined together, said second web of material having a second yield to break point under tensile forces that is lower than the yield to break point of said carrier web;
(c) providing an apparatus for mechanically straining said composite web, said apparatus having at least one patterned surface thereon; and
(d) subjecting said composite web to a mechanical straining process using said apparatus by impressing the at least one patterned surface thereon so that the second web of material is at least partially formed into particulate material without forming the carrier web into particulate material.

19. A method of making a self-contained web of particulate material, said method comprising the steps of:
(a) providing a carrier web in the form of a web having a first yield to break point under tensile forces;
(b) providing a second web of material for forming into particulate material on said carrier web to form a composite web, said second web of material having a second yield to break point under tensile forces that is lower than the yield to break point of said carrier web;
(c) providing an apparatus wherein said apparatus comprises: (i) a first patterned roll having said at least one patterned surface thereon; (ii) a second patterned roll having a patterned surface thereon; (iii) a roll with a compressible and resilient surface that forms a pressure biased nip with said first and second patterned rolls; and (iv) the composite web is successively fed through a nip between the first patterned roll and the roll with the compressible and resilient surface and the second patterned roll and the roll with the compressible and resilient surface for mechanically straining said composite web, said apparatus having at least one patterned surface thereon; and
(d) subjecting said composite web to a mechanical straining process using said apparatus by impressing the at least one patterned surface thereon so that the second web of material is at least partially formed into particulate material without forming the carrier web into particulate material.

20. A method of making a self-contained web of particulate material, said method comprising the steps of:
(a) providing a carrier web in the form of a web having a first yield to break point under tensile forces;
(b) providing a second web of material for forming into particulate material on said carrier web to form a composite web, said second web of material having a second yield to break point under tensile forces that is lower than the yield to break point of said carrier web;
(c) providing an apparatus for mechanically straining said composite web wherein said apparatus, said apparatus having at least one patterned surface thereon; and said apparatus comprises two sets of rolls each having teeth thereon that are partially intermeshin, said sets of rolls comprising:
(i) a first pair of rolls having ridges and valleys that are disposed around the circumference of the rolls, and said ridges form said teeth; and
(ii) a second pair of rolls, each roll in said second pair of rolls having an axis, said rolls in said second pair of rolls having ridges and valleys that run parallel to the axes of said second pair of rolls, and said ridges on said second pair of rolls form said teeth on said second pair of rolls: and
(d) subjecting said composite web to a mechanical straining process using said apparatus by impressing the at least one patterned surface thereon so that the second web of material is at least partially formed into particulate material without forming the carrier web into particulate material.

21. The method of claim 20 wherein said composite web is fed sequentially through a nip between said first pair of rolls and a nip between said second pair of rolls.

22. The method of claim 20 wherein said composite web is fed sequentially through a nip between said second pair of rolls and a nip between said first pair of rolls.

23. A method of making an elastic absorbent composite structure in a process of making at least a portion of an absorbent article, said method comprising the steps of:
(a) providing an elastic material having two surfaces, each of which generally defines a plane, said elastic material having a first yield to break point under tensile forces;
(b) providing an absorbent second material, which is placed parallel to the planes defined by the surfaces of said elastic material to form a composite structure, said absorbent second material having a second yield to break point under tensile forces that is lower than the yield to break point of said elastic material, and said composite structure having two surfaces, and edges;
(c) providing an apparatus for mechanically straining said composite structure, said apparatus having at least one patterned surface thereon; and
(d) subjecting said composite structure to a mechanical straining process using said apparatus by impressing the at least one patterned surface into said composite structure with a force that is greater than the second yield to break point, but less than said first yield to break point so that the absorbent second material is at least partially slit without slitting the elastic material.

24. The method of claim 23 wherein said elastic material comprises an elastic polyurethane foam.

25. The method of claim 23 further comprising providing a second material, and the step (b) further comprises placing one of said elastic materials on each side of said absorbent second material.

26. The method of claim 23 further comprising providing a liquid pervious topsheet material adjacent to one surface of said composite structure, and a liquid impervious backsheet material adjacent to the other surface of said composite structure, wherein said topsheet and said backsheet extend beyond the edges of said composite structure, and are at least partially peripherally joined together prior to the step (d) of subjecting said composite structure to a mechanical straining process.

27. A method of slitting an absorbent material in situ on another material in a process of making at least a portion of an absorbent article, said method comprising the steps of:
(a) providing a carrier material having a first yield to break point under tensile forces, said first yield to break point being the point at which said carrier material completely severs into strips;

(b) providing an absorbent second material on said carrier web to form a composite structure, said second material having a second yield to break point under tensile forces that is lower than the first yield to break point of said carrier material, said composite structure having two surfaces;

(c) providing an apparatus for mechanically straining said composite structure, said apparatus having at least one patterned surface thereon; and (d) subjecting said composite structure to a mechanical straining process using said apparatus by impressing the at least one patterned surface into at least a portion of at least one of the surfaces of said composite structure with a force that is great enough to partially slit said carrier material and greater than the second yield to break point, but less than said first yield to break point so that the absorbent second material is slit and the carrier material is only partially slit.

28. The method of claim 27 wherein the partial slits in said carrier material are intermittent and vertically aligned with portions of the slits in said absorbent second material.

* * * * *